(12) United States Patent
Traversa et al.

(10) Patent No.: US 8,673,347 B2
(45) Date of Patent: Mar. 18, 2014

(54) POLYMER CONJUGATES OF K-252A AND DERIVATIVES THEREOF

(75) Inventors: Silvio Traversa, Palazzo Canavese (IT); Raffaella Bagnod, Bollengo (IT); Domenico Barone, Turin (IT); Luisa Bertarione Rava Rossa, Pavon Canavese (IT); Silvano Fumero, Ivrea (IT); Valentina Mainero, Ivrea (IT); Alessandra Marconi, Reggio Emilia (IT); Cecilia Oderda, Vésenaz (CH); Carlo Pincelli, Sassuolo (IT); Chiara Lorenzetto, Villafranca Piemonte (IT); Luca Beccaria, Ivrea (IT)

(73) Assignee: Creabilis Therapeutics S.p.A., Colleretto Giacosa (IT)

( * ) Notice: Subject to any disclaimer, the term of this patent is extended or adjusted under 35 U.S.C. 154(b) by 1236 days.

(21) Appl. No.: 12/064,461

(22) PCT Filed: Aug. 25, 2006

(86) PCT No.: PCT/EP2006/008374
§ 371 (c)(1),
(2), (4) Date: Feb. 22, 2008

(87) PCT Pub. No.: WO2007/022999
PCT Pub. Date: Mar. 1, 2007

(65) Prior Publication Data
US 2008/0193517 A1    Aug. 14, 2008

Related U.S. Application Data

(60) Provisional application No. 60/710,890, filed on Aug. 25, 2005, provisional application No. 60/720,454, filed on Sep. 27, 2005, provisional application No. 60/811,469, filed on Jun. 7, 2006.

(51) Int. Cl.
*A61K 31/787* (2006.01)
*C08G 73/06* (2006.01)
*A61K 9/127* (2006.01)
*A61P 35/00* (2006.01)

(52) U.S. Cl.
USPC .................. 424/450; 424/78.36; 528/423

(58) Field of Classification Search
USPC ................ 424/450, 78.36; 528/423
See application file for complete search history.

(56) References Cited

U.S. PATENT DOCUMENTS 5,461,146 A * 10/1995 Lewis et al. ............... 540/545
2003/0170765 A1 * 9/2003 Rouhani et al. ............ 435/7.92
2006/0128793 A1 * 6/2006 Zask et al. .................. 514/453

FOREIGN PATENT DOCUMENTS

| EP | 0 303 697 A1 | 2/1989 | |
|---|---|---|---|
| WO | 0185151 A2 | 11/2001 | |
| WO | WO 01/85151 | * 11/2001 | ............. A61K 31/00 |
| WO | 02/074337 A1 | 9/2002 | |
| WO | 2006/010628 A1 | 2/2006 | |

OTHER PUBLICATIONS

Pasut et al. Expert Opin. Ther. Patents, vol. 14(6) pp. 859-894 2004.*
Dictoinary.com (Steric hindrance) http://dictionary.reference.com/browse/steric+hindrance. 2012.*
Long et al., "Non-camptothecin topoisomerase I active compounds as potential anticancer agents", Expert Opinion on Therapeutic Patents 2000, vol. 10, No. 5, 2000, pp. 635-666.
Pasut et al., "Protein, Peptide and Non-Peptide Drug Pegylation for Therapeutic Application", Expert Opinion on Therapeutic Patents, vol. 14, No. 6, 2004, pp. 859-894.
Third party submission filed in the corresponding European Application No. EP 06 777 076.8 (published as EP 1 919979) on Sep. 6, 2011, 3 pages.
Third party submission filed in the corresponding European Application No. EP 1919979, dated Oct. 11, 2001, 2 pages.
Viegas et al., "Regulatory strategy and approval processes considered for PEG-drug conjugates and other nanomedicines", PEGylated Protein Drugs: Basic Science and Clinical Applications, 2009, pp. 273-281.

* cited by examiner

Primary Examiner — Anoop Singh
Assistant Examiner — Anna Falkowitz
(74) Attorney, Agent, or Firm — Rothwell, Figg, Ernst & Manbeck, P.C.

(57) ABSTRACT

The present invention relates to novel polymer conjugates of K-252a and derivatives thereof and to their use for the preparation of a pharmaceutical composition useful for the prevention, alleviation and treatment of kinase-associated pathologies. In particular, the present invention relates to the prevention, alleviation and treatment of HMGB1-associated pathologies. The invention relates to the use of the novel polymer conjugates of K-252a and derivatives thereof in the preparation of a pharmaceutical composition useful for the prevention, alleviation and treatment of a) neurological disorders, neuropathies and neurodegenerative disorders of the central and peripheral nervous system; b) dermal pathologies, in particular dermal pathologies associated with an excessive keratinocyte proliferation, in particular psoriasis; and c) NGF-related pain. More specifically, the present invention relates to a polymer conjugate of K-252a and derivatives thereof, wherein the polymer is polyethylene glycol or methoxy-polyethylene glycol formula (I).

17 Claims, 19 Drawing Sheets

Figure 9a

Table a: Tyrosine kinase inhibition by K-252a

| Kinase | K-252a (200 nM) | Ref. | Ref. cpd (nM) |
|---|---|---|---|
| ABL | -14.2 | 86.2 | Staurosporine (1000) |
| ARG | 0.1 | 89.6 | Staurosporine (3000) |
| TNK1 | 94.8 | 89.2 | Staurosporine (3) |
| ALK | 69.5 | 93.8 | Staurosporine (30) |
| AXL | 51.5 | 85.1 | Staurosporine (3000) |
| MER | 80.8 | 90.7 | Staurosporine (100) |
| CSK | 43.0 | 88.8 | Staurosporine (300) |
| EGFR | 16.4 | 91.4 | Staurosporine (10000) |
| HER2 | 7.7 | 65.6 | Staurosporine (10000) |
| HER4 | 39.4 | 94.1 | Staurosporine (10000) |
| EphA2 | 8.9 | 93.7 | Staurosporine (10000) |
| EphB2 | 0.4 | 83.7 | Staurosporine (1000) |
| EphB4 | 13.3 | 92.7 | Staurosporine (10000) |
| FAK | 53.5 | 90.4 | Staurosporine (100) |
| FGFR1 | 57.9 | 91.4 | Staurosporine (100) |
| FGFR2 | 67.2 | 96.7 | Staurosporine (100) |
| IGF1R | 40.6 | 98.6 | Staurosporine (3000) |
| INSR | 38.0 | 93.3 | Staurosporine (1000) |
| JAK1 | 83.1 | 82.8 | Staurosporine (30) |
| JAK2 | 99.5 | 96.3 | Staurosporine (3) |
| JAK3 | 100.4 | 97.8 | Staurosporine (3) |
| TYK2 | 98.1 | 94.5 | Staurosporine (3) |
| MET | 83.2 | 87.0 | Staurosporine (300) |
| RON | 5.2 | 81.6 | Staurosporine (10000) |
| FLT3 | 95.8 | 94.0 | Staurosporine (3) |
| CSFR | 55.7 | 89.1 | Staurosporine (30) |
| KIT | 87.3 | 96.7 | Staurosporine (10) |
| PDGFRα | 96.1 | 93.5 | Staurosporine (3) |
| PDGFRβ | 98.1 | 98.7 | Staurosporine (0.3) |
| RET | 94.2 | 88.1 | Staurosporine (30) |

Figure 9a (continued)

| Kinase | K-252a (200 nM) | Ref. | Ref. cpd (nM) |
|---|---|---|---|
| BLK | 83.5 | 94.9 | Staurosporine (30) |
| BRK | 35.8 | 87.4 | Staurosporine (10000) |
| FGR | 85.6 | 88.7 | Staurosporine (10) |
| FYN | 67.2 | 98.9 | Staurosporine (100) |
| HCK | 68.2 | 96.1 | Staurosporine (30) |
| LCK | 65.2 | 97.6 | Staurosporine (100) |
| LYNa | 58.9 | 95.2 | Staurosporine (100) |
| LYNb | 51.2 | 96.4 | Staurosporine (100) |
| SRC | 20.6 | 90.0 | Staurosporine (3000) |
| SRM | 0.4 | 74.0 | Staurosporine (10000) |
| YES | 65.1 | 94.1 | Staurosporine (30) |
| TrkA | 97.6 | 93.4 | Staurosporine (3) |
| TrkB | 98.2 | 67.3 | Staurosporine (0.3) |
| TrkC | 94.4 | 86.2 | Staurosporine (10) |
| FLT1 | 73.9 | 94.8 | Staurosporine (300) |
| KDR | 62.9 | 87.7 | Staurosporine (300) |

Table b: Serine/threonine kinase inhibition by K-252a

| Kinase | K-252a (200 nM) | Ref. | Ref. cpd (nM) |
|---|---|---|---|
| PKACα | 69.4 | 94.9 | Staurosporine (30) |
| PKCα | 64.4 | 97.8 | Staurosporine (30) |
| PKCε | 60.9 | 98.8 | Staurosporine (3) |
| PKCγ | 53.3 | 94.3 | Staurosporine (10) |
| CaMK4 | 0.0 | 88.4 | Staurosporine (3000) |
| CaMK2α | 83.9 | 92.9 | Staurosporine (30) |
| CHK1 | 92.8 | 91.1 | Staurosporine (10) |
| MAPKAPK2 | 44.3 | 90.5 | Staurosporine (1000) |
| CHK2 | 93.9 | 97.1 | Staurosporine (300) |
| CDK/CycA | 75.5 | 95.7 | Staurosporine (30) |

Figure 9a (continued)

| Kinase | K-252a (200 nM) | Ref. | Ref. cpd (nM) |
|---|---|---|---|
| Erk1 | 32.0 | 80.2 | 5-Iodotubericidin (10000) |
| Erk2 | 14.2 | 62.1 | 5-Iodotubericidin (10000) |
| JNK1 | 94.3 | 82.1 | JNK Inhibitor II (300) |
| JNK2 | 91.4 | 92.8 | JNK Inhibitor II (300) |
| p38α | -1.5 | 87.9 | SB202190 (300) |
| p38β | -0.2 | 55.7 | SB202190 (300) |
| AurA | 91.9 | 84.9 | Staurosporine (30) |
| IKKβ | 2.7 | 47.9 | Staurosporine (10000) |
| MAP2K3 | 100.0 | 84.5 | Staurosporine (30) |
| MAP2K7 | 68.2 | 85.8 | Staurosporine (3000) |
| IRAK4 | 51.9 | 95.9 | Staurosporine (10000) |

Figure 9b

Table a: Tyrosine kinase inhibition by CT327

| Kinase | CT327 (200 nM) | Ref. | Ref. cpd (nM) |
|---|---|---|---|
| ABL | 2.2 | 89.3 | Staurosporine (1000) |
| ARG | 1.6 | 90.7 | Staurosporine (3000) |
| TNK1 | 13.0 | 84.0 | Staurosporine (3) |
| ALK | 9.5 | 93.9 | Staurosporine (30) |
| AXL | -2.2 | 90.3 | Staurosporine (3000) |
| MER | -0.1 | 84.2 | Staurosporine (100) |
| CSK | 1.0 | 91.0 | Staurosporine (300) |
| EGFR | 2.9 | 85.3 | Staurosporine (10000) |
| HER2 | -1.4 | 37.8 | Staurosporine (10000) |
| HER4 | 5.3 | 88.2 | Staurosporine (10000) |
| EphA2 | -4.8 | 87.7 | Staurosporine (10000) |
| EphB2 | -2.9 | 83.6 | Staurosporine (1000) |
| EphB4 | 15.1 | 83.5 | Staurosporine (10000) |
| FAK | 3.8 | 84.5 | Staurosporine (100) |
| FGFR1 | 1.0 | 90.0 | Staurosporine (100) |
| FGFR2 | 6.0 | 95.8 | Staurosporine (100) |
| IGF1R | 4.5 | 90.4 | Staurosporine (3000) |
| INSR | 3.0 | 92.8 | Staurosporine (1000) |
| JAK1 | 3.1 | 90.8 | Staurosporine (30) |
| JAK2 | 30.9 | 96.0 | Staurosporine (3) |
| JAK3 | 27.1 | 86.7 | Staurosporine (3) |
| TYK2 | 16.2 | 90.4 | Staurosporine (3) |
| MET | 6.2 | 73.8 | Staurosporine (300) |
| RON | -0.7 | 69.1 | Staurosporine (10000) |
| FLT3 | 24.7 | 85.9 | Staurosporine (3) |
| CSFR | -5.7 | 87.8 | Staurosporine (30) |
| KIT | -3.3 | 96.7 | Staurosporine (10) |
| PDGFRα | 7.7 | 91.6 | Staurosporine (3) |
| PDGFRβ | 13.9 | 80.9 | Staurosporine (0.3) |
| RET | 8.0 | 88.9 | Staurosporine (30) |

Figure 9b (continued)

| Kinase | CT327 (200 nM) | Ref. | Ref. cpd (nM) |
|---|---|---|---|
| BLK | 11.1 | 94.1 | Staurosporine (30) |
| BRK | -5.4 | 71.3 | Staurosporine (10000) |
| FGR | -0.2 | 85.3 | Staurosporine (10) |
| FYN | -5.1 | 95.6 | Staurosporine (100) |
| HCK | -3.1 | 90.2 | Staurosporine (30) |
| LCK | 15.9 | 96.5 | Staurosporine (100) |
| LYNa | 6.9 | 94.8 | Staurosporine (100) |
| LYNb | 2.2 | 93.0 | Staurosporine (100) |
| SRC | 4.7 | 86.7 | Staurosporine (3000) |
| SRM | -0.8 | 61.4 | Staurosporine (10000) |
| YES | 5.0 | 85.8 | Staurosporine (30) |
| TrkA | 55.0 | 88.0 | Staurosporine (3) |
| TrkB | 11.6 | 46.1 | Staurosporine (0.3) |
| TrkC | 16.3 | 86.3 | Staurosporine (10) |
| FLT1 | 3.9 | 94.6 | Staurosporine (300) |
| KDR | 7.5 | 90.8 | Staurosporine (300) |

Table b: Serine/threonine kinase inhibition by CT327

| Kinase | CT327 (200 nM) | Ref. | Ref. cpd (nM) |
|---|---|---|---|
| AKT2 | 0.9 | 90.7 | Staurosporine (1000) |
| PKACα | -1.8 | 93.8 | Staurosporine (30) |
| PKCα | -2.0 | 96.1 | Staurosporine (30) |
| PKCε | 0.7 | 102.1 | Staurosporine (3) |
| PKCγ | -2.1 | 94.3 | Staurosporine (10) |
| CaMK4 | 0.5 | 87.9 | Staurosporine (3000) |
| CaMK2α | 0.9 | 96.1 | Staurosporine (30) |
| CHK1 | 4.8 | 93.5 | Staurosporine (10) |
| MAPKAPK2 | -0.3 | 81.6 | Staurosporine (1000) |
| CHK2 | 3.0 | 98.1 | Staurosporine (300) |

Figure 9b (continued)

| Kinase | CT327 (200 nM) | Ref. | Ref. cpd (nM) |
|---|---|---|---|
| CDK/CycA | -7.8 | 95.0 | Staurosporine (30) |
| Erk1 | -4.2 | 76.9 | 5-Iodotubericidin (10000) |
| Erk2 | 3.6 | 67.5 | 5-Iodotubericidin (10000) |
| JNK1 | 3.9 | 55.3 | JNK Inhibitor II (300) |
| JNK2 | 4.0 | 90.8 | JNK Inhibitor II (300) |
| JNK3 | 14.7 | 89.7 | JNK Inhibitor II (1000) |
| p38α | -1.9 | 92.3 | SB202190 (300) |
| p38β | 4.4 | 81.1 | SB202190 (300) |
| AurA | -1.1 | 85.5 | Staurosporine (30) |
| IKKβ | -2.7 | 53.8 | Staurosporine (10000) |
| MAP2K1 | 6.1 | 65.0 | Staurosporine (3) |
| MAP2K3 | 40.7 | 78.0 | Staurosporine (100) |
| MAP2K7 | 8.5 | 92.5 | Staurosporine (300) |
| IRAK4 | -11.1 | 98.6 | Staurosporine (10000) |

| Source of Variation | % of total variation | P value | |
|---|---|---|---|
| Interaction | 7.46 | 0.0003 | *** |
| Treatment | 1.63 | 0.0044 | ** |
| Time (hours) | 78.49 | P<0.0001 | *** |

| Source of Variation | % of total variation | P value | |
|---|---|---|---|
| Interaction | 19.75 | 0.0005 | *** |
| Treatment | 3.30 | 0.0145 | * |
| Time (hours) | 42.82 | P<0.0001 | *** |

| Source of Variation | % of total variation | P value | |
|---|---|---|---|
| Interaction | 15.72 | P<0.0001 | *** |
| Tretment | 3.27 | 0.0007 | *** |
| Time (hours) | 65.94 | P<0.0001 | *** |

| Source of Variation | % of total variation | P value | |
|---|---|---|---|
| Interaction | 1.67 | 0.0010 | *** |
| Treatment | 0.60 | 0.0008 | *** |
| Time (hours) | 94.49 | P<0.0001 | *** |

| Source of Variation | % of total variation | P value | |
|---|---|---|---|
| Interaction | 20.65 | P<0.0001 | *** |
| Treatment | 4.75 | 0.0013 | ** |
| Time (hours) | 50.55 | P<0.0001 | *** |

POLYMER CONJUGATES OF K-252A AND DERIVATIVES THEREOF

CROSS REFERENCE TO RELATED APPLICATION

This application is a 35 U.S.C. 371 National Phase Entry Application from PCT/EP2006/008374, filed Aug. 25, 2006, which claims the benefit of U.S. Provisional Application Nos. 60/710,890, 60/720,454 and 60/811,469 filed on Aug. 25, 2005, Sep. 27, 2005 and Jun. 7, 2006, respectively, the disclosures of which are incorporated herein in their entirety by reference.

The present invention relates to novel polymer conjugates of K-252a and derivatives thereof and to their use for the preparation of a pharmaceutical composition useful for the prevention, alleviation and treatment of kinase-associated pathologies. In particular, the present invention relates to the prevention, alleviation and treatment of HMGB1-associated pathologies. In a particular aspect, the invention relates to the use of the novel polymer conjugates of K-252a and derivatives thereof in the preparation of a pharmaceutical composition useful for the prevention, alleviation and treatment of neurological disorders, neuropathies and neurodegenerative disorders of the central and peripheral nervous system. In a further preferred aspect, the invention relates to the use of the polymer conjugates in the preparation of a pharmaceutical composition useful for the prevention, alleviation and treatment of dermal pathologies, in particular dermal pathologies associated with an excessive keratinocyte proliferation, in particular psoriasis. In a still further aspect, the invention relates to the use of the polymer conjugates in the prevention, alleviation and treatment of NGF-related pain. More specifically, the present invention relates to a polymer conjugate of K-252a and derivatives thereof, wherein the polymer is polyethylene glycol or methoxy-polyethylene glycol.

K-252a is a lipophilic alkaloid for the first time isolated from *Nocardiopsis* sp soil fungi (WO 97/38120), having a indolocarbazole skeleton represented by the following formula:

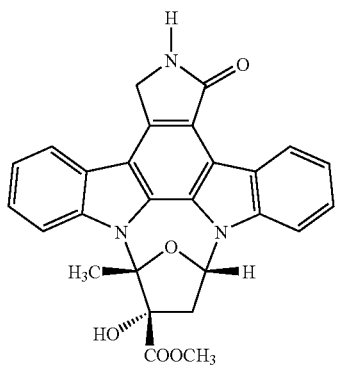 [SMILES: COC(=O)[C@]1(O)C[C@@H]2O[C@@]1(C)n1c3ccccc3c3c4c(c5c6ccccc6n2c5c31)C(=O)NC4]

K-252a strongly inhibits protein kinase C (PKC), which plays a central role in regulating cell functions, and has various activities such as the action of inhibiting smooth muscle contraction (Jpn. 3. Pharmacol. 43(suppl.): 284, 1987), the action of inhibiting serotonin secretion (Yamada et al., Biochem. Biophys. Res. Commun. 144:35-40, 1987), the action of inhibiting elongation of neuraxone (Koizumi et al., J. Neurosci. Res. 8:715, 1988), the action of inhibiting histamine release (Morita et al., Allergy 43:100-104, 1988), the action of inhibiting smooth muscle myosin light-chain kinase (Nakanishi et al., J. Biol. Chem. 263:6215-6219, 1988), anti-inflammatory action (Papp et al., Acta Physiol. Hung. 80: 423-425, 1992), the activity of cell survival (Glicksman et al., J. Neurochem. 64:1502-1512, 1995), etc. It has also been disclosed in Grove et al., Exp. Cell Res., 193: 175-182, 1991 that K-252a has the activity of inhibiting IL-2 production. The complete synthesis of K-252a has been achieved (Wood et al., J. Am. Chem. Soc. 117:10413-10414, 1995) as well.

Nerve growth factor (NGF) is the best characterized neurotrophin and is required for normal development and function of certain sensory and cholinergic neurons (Levi-Montalcini, Annu. Rev. Neurosci. 5:341-362, 1982). The high-affinity neurotrophic receptors, trks, comprise a family of proteins consisting of trk A, trk B, and trk C (Knusel et al., J. Neurochem. 59:715-722, 1992). Members of this receptor family are membrane-associated proteins that exhibit tyrosine kinase activity. Interaction of a neurotrophin ligand with trks induces phosphorylation of specific tyrosine residues on the receptor. Phosphorylation of trks is an immediate response to neurotrophin binding. It is an absolute requirement for the activation of enzymatic pathways regulating functional responses to the neurotrophins by the cell (Klein et al., Cell 65:189-197, 1991; Lamballe et al., Cell 66:967-979, 1991). K-252a is an inhibitor of several enzymes, including trks. Consistent with this effect, K-252a blocks NGF-mediated cell survival in some in vitro cell assays (Koizumi et al., J. Neurosci. 8:715-721, 1988; Doherty et al., Neurosci. Lett. 96:1-6, 1989; Matsuda et al., Neurosci. Lett. 87:11-17, 1988), since it influences the phosphorylation state of trks.

In literature, the therapeutic potential of K-252a and derivatives thereof, as, for example, the bis-ethyl-thiomethyl analogue CEP-1347 in neurodegenerative diseases has been shown (Annu Rev Pharmacol Toxicol. 2004; 44:451-74; Neurochem Int. 2001 November-December; 39(5-6):459-68; Neuroport. 2000 Nov. 9; 11(16): 3453-6; Neuroscience. 1998 September; 86(2):461-72; Brains Res. 1994 Jul. 4; 650(1): 170-4).

Keratinocytes, a key cellular component both for homeostasis and pathophysiologic processes of the skin, secrete a number of cytokines and are stimulated by several growth factors. NGF is synthesized in the skin and significantly stimulates the proliferation of normal human keratinocytes in culture in a dose-dependent manner. This effect can be prevented by the addition of K-252a, which is a high-affinity NGF receptor (trk) specific inhibitor, thus suggesting that NGF effect on human keratinocytes is mediated by the high-affinity NGF receptor. So NGF could act as a cytokine in human skin and take part in disorders of keratinocyte proliferation (Pincelli et al., J. Invest. Dermatol. 103:13-18, 1994). Neurogenic inflammation and the role of NGF have been extensively studied in psoriasis. There are increased levels of NGF in the keratinocytes and upregulation of NGF receptor in the cutaneous nerves of psoriatic plaques. NGF can influence all the salient pathologic events noticed in psoriasis such as proliferation of keratinocytes, angiogenesis, T cell activation, expression of adhesion molecules, proliferation of cutaneous nerves, and upregulation of neuropeptides. In a double-blinded, placebo-controlled study, the role of NGF and NGF receptor in psoriasis was addressed in an in vivo system using the severe combined immunodeficient (SCID) mouse-human skin model of psoriasis. The transplanted psoriatic plaques on the SCID mice were treated with K-252a. Psoriasis significantly improved following 2 weeks of therapy. (Raychaudhuri et al., J. Invest. Dermatol. 122:812-819, 2004).

It has been further reported that NGF has a crucial role in the generation of pain and hyperalgesia in several acute and chronic pain states. The expression of NGF is high in injured and inflamed tissues, and activation of the NGF receptor tyrosine kinase TrkA on nociceptive neurons triggers and potentiates pain signaling by multiple mechanisms. NGF antagonism is expected to be a highly effective therapeutic approach in many pain states, and to be free of the adverse effects of traditional analgesic drugs [Hefti F F et al. *Trends Pharmacol. Sci.* (2006) 27:85-91]. Evidence indicates that TrkA receptors are required for the nociceptive actions of NGF. Most of the receptor tyrosine kinase inhibitors block the binding of ATP to the catalytic tyrosine kinase domain [Madhusudan S et al. *Clin. Biochem.* (2004) 37: 618-635]. The alkaloid K-252a inhibits Trk signaling with high potency and attenuates hypersensitivity in an animal model of pancreatic pain [Winston J H et al. *J. Pain* (2003) 4:329-337]. However, K-252a lacks selectivity for TrkA since it is a potent inhibitor for several kinases. This means that K-252a is likely to have many adverse effects that are unrelated to inhibition of TrkA.

The patent application WO 2005/014003 describes the use of tyrosine kinase inhibitors of microbial origin belonging to the K-252 family to prepare topical medicaments able to inhibit the excessive keratinocyte proliferation characteristic of disorders such as psoriasis and skin tumors.

The International Patent Application PCT/EP2005/008258 discloses the use of K-252a and derivatives thereof in the prevention and treatment of HMGB1-associated pathologies. HMGB1 is a pro-inflammatory chemokine released by necrotic or dying cells, leading to an inflammatory cytokine cascade in several human pathologies. In a preferred embodiment the above mentioned US Patent Applications describe the novel use of K-252a and derivatives thereof as therapeutic agent for the prevention and treatment of restenosis. K-252a has in fact the ability of blocking/inhibiting HMGB1-induced arterial smooth muscle cell migration and proliferation, events that are both at the basis of restenosis formation. To this end, K-252a and derivatives thereof are loaded as surface-coating by binding, embedding or adsorbing on a medical device, in particular on a stent, in order to have the active agent released in situ.

In addition to K-252a itself, various derivatives of K-252a have been synthesized and tested for biological activity. As an example, CEP1347, a K252a derivative, retains neuroprotective properties but does not inhibit TrkA. CEP1347 has been shown to directly inhibit MAPKKKs, including MLK3 (Roux et al., J. Biol. Chem. 277:49473-49480, 2002). Another K-252a derivative, KT5926, has been investigated against vesicular stomatitis virus (VSV) replication in BHK-21 cells (Kim et al., Biol. Pharm. Bull. 21:498-505, 1998). It is known that K-252a analogs with conservative substitutions at C3' retain potency against a range of kinases (Schneider et al., Org. Lett. 7:1695-1698, 2005).

The efficacy of systemically administered drugs may be hampered in vivo by factors such as poor solubility at physiologic pH and rapid elimination by glomerular filtration, cellular clearance and metabolism. In many cases, such disadvantageous effects prevent an effective therapeutic use of such agents. A successful strategy for improving both efficacy and duration of the agents' effects and for reducing potential toxicologic effects is the covalent binding of a biologically active agent to diverse polymers. One of the polymers that is most often used for improving the pharmacologic and toxicologic properties of an active agent is the polyalkylenoxide polyethylene gylcol, PEG in short.

Polyethylene glycol (PEG) polymers, which are amphiphilic, nontoxic, and immunologically inert, can be conjugated to pharmaceuticals to manipulate many of the pharmacokinetic and toxicologic properties. In the area of drug delivery, PEG derivatives have been widely used in covalent attachment (i.e., "PEGylation") to proteins in order to reduce immunogenicity, proteolysis and kidney clearance and to enhance solubility (Zalipsky, Adv. Drug Del. Rev. 16:157-182, 1995). Similarly, PEG has been attached to low molecular weight, relatively hydrophobic drugs in order to reduce toxicity, alter biodistribution, and enhance solubility. Pegylated pharmaceuticals may be more effective than their unmodified parent drugs by virtue of the properties of PEG that are transferred to the conjugates (Molineux, Pharmacotherapy 23:3 S-8S, 2003).

The aim of the present invention was to exploit the peculiar characteristics of some polymers, in particular of polyethylene glycol (PEG) in order to develop therapeutically useful administration forms of members of the indolocarbazole family. It was the aim of the inventors of the invention to obtain through the PEG modification an improved pharmacokinetic and toxicologic performance of the polymer conjugated indolocarbazole compound. Moreover, a change in the activity and/or toxicity profile of the new conjugated compounds was the focus of the invention, too.

One of the specific problems underlying the present invention was to exploit the peculiar characteristics of some polymers, in particular of PEG, in order to develop administration forms of K-252a which permit an improved pharmacokinetic and toxicologic performance, achieving the best bioavailability of K-252a or of its derivative in the various possible application routes. In a particular aspect of the present invention, the problem was to exploit the characteristics of the polymer in order to achieve, in case of a topical administration, a decreased absorption of K-252a or its derivatives and therefore a reduction and even elimination of possible systemic toxicity and/or side effects.

The present invention is therefore directed to novel polymer conjugates of members of the indolocarbazole compounds and in particular of K-252a or of derivatives thereof, their preparation and their use, wherein the polymer conjugate has an increased water solubility, an improved pharmaceutical manageability, an improved pharmacokinetic and bioavailability and/or a decreased toxicity and/or immunogenicity in comparison to the non-conjugated indolocarbazole compounds or to the K-252a compound or derivatives thereof.

In a particular preferred aspect, the present invention is directed to a polymer conjugate of K-252a or of derivatives thereof, their preparation and their use, wherein, after topical administration, the systemic absorption is limited and therefore the systemic toxicity and/or side-effects are reduced or even eliminated.

A first aspect of the present invention is therefore a polymer conjugate of an indolocarbazole compound of the general formula (I):

Formula (I)

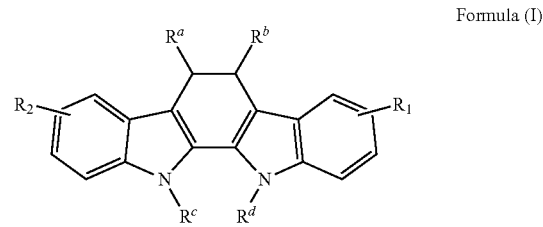

and preferably of general formula (II)

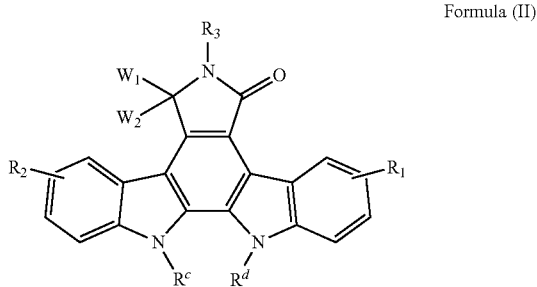

Formula (II)

wherein $R^a$ and $R^b$ are independently a hydrogen or an organic residue selected from the group consisting of substituted or unsubstituted lower alkyl, substituted or unsubstituted lower alkenyl, substituted or unsubstituted lower alkynyl, hydroxy, lower alkoxy, carboxy or alcoxycarbonyl; or $R^a$ and $R^b$ together form a 5-7 member, preferably 5 member cyclic structure fused directly to the indolo[2,3-a]carbazole nucleus structure, containing 0, 1 or 2 heteroatoms, preferably nitrogen atoms, and optionally containing a carbonyl group and the cyclic structure being unsubstituted or substituted, preferably by at least one substituent group selected from a carbonyl group or W1 or W2 and wherein if a heteroatom member of the cyclic structure is nitrogen, the nitrogen is substituted by the residue $R_3$;

and wherein $R^c$ and $R^d$ are (a) independently hydrogen or an organic residue selected from the group consisting of substituted or unsubstituted lower alkyl, substituted or unsubstituted lower alkenyl, substituted or unsubstituted lower alkynyl, hydroxy, lower alkoxy, carboxy or alkoxycarbonyl; or one of $R^c$ and $R^d$ is selected from hydrogen, substituted or unsubstituted lower alkyl and hydroxy, while the other one of $R^c$ and $R^d$ is a 3-7 member, preferably a 5 or 6 member cyclic moiety, preferably a cyclic carbohydrate moiety, wherein the cyclic moiety is unsubstituted or substituted, preferably substituted by at least one functional group suitable for conjugation of a polymeric moiety, more preferably substituted in at least one, preferably 2 to 3 and up to all positions of the cycle by hydroxy, substituted or unsubstituted lower alkyl, lower alkoxy, carboxy, alkoxycarbonyl, amino, lower alkylamino, lower alkylaminocarbonyl or oxime group; or (b) $R^c$ and $R^d$ together form a 3-7 member, preferably a 5 or 6 member cyclic moiety, preferably a cyclic carbohydrate moiety, wherein the cyclic moiety is unsubstituted or substituted, preferably substituted by at least one functional group suitable for conjugation of a polymeric moiety, more preferably substituted in at least one, preferably two or three, and up to all positions of the cycle by hydroxy, substituted or unsubstituted lower alkyl, lower alkoxy, carboxy, alcoxycarbonyl, amino, lower alkylamino, lower alkylaminocarbonyl and/or oxime group, and wherein the residues $R_1$, $R_2$, $R_3$, $W_1$ and $W_2$ are defined as described below;

or a pharmaceutically acceptable salt thereof.

The compounds (I) and (II) have at least one functional group to which a polymeric moiety is conjugated, preferably located on the radical $R_c$ and/or $R_d$. The conjugate may comprise one or several polymeric moieties, e.g. one, two, three or more polymeric moieties. Preferably the conjugate compounds of the present invention comprise one polymeric moiety.

The 3-7 member cyclic moiety, preferably the cyclic carbohydrate moiety is bond to the indolocarbazole compound by attachment to one indole nitrogen or by attachment to both indole nitrogens of the indolocarbazole structure. Hence, the attachment can include a single indole or two indoles and is preferably provided by one or two N-glycosidic linkages.

Preferably, the 3-7 member cyclic moiety, preferably the cyclic carbohydrate moiety, is a substituted furano or a substituted pyrano group. Hence, the preferred polymer conjugated compounds are cyclofuranosylated indolocarbazole compounds or cyclopyranosylated indolocarbazole compounds. Preferred cyclofuranosylated indolocarbazole compounds which according to the invention are conjugated to a polymer moiety may be selected from K-252a, K-252b, ICP-1. Preferred cyclopyranosylated indolocarbazole compounds may be selected from Staurosporine, K-252d, TAN-1030a, RK-286c, MLR-52, Rebeccamycin, UNC-01, UNC-02 and RK-1409B.

The at least one polymeric moiety is conjugated to the compound of formulae (I) and/or (II) by a covalent chemical linkage in order to provide a stable conjugate. In particular, the polymer moiety is bond to the compounds of general formulae (I) and/or (II) by attachment on a functional group selected from hydroxy, amino, carboxy, alkoxycarbonyl or aminocarbonyl. In the very preferred embodiment of the invention, the polymer moiety is attached to the compound of general formulae (I) and/or (II) on one of the residues $R^c$ and $R^d$, particularly preferably on the cyclic carbohydrate moiety identified by the residues $R^cC$ and $R^d$. The polymer moiety of the compound of the invention as well as the preferred chemical linkage by which the polymer may be attached to the indolocarbazole compound of formulae (I) and/or (II) are described below.

A very preferred aspect of the present invention is a polymer conjugate, which is represented by the following formula (III):

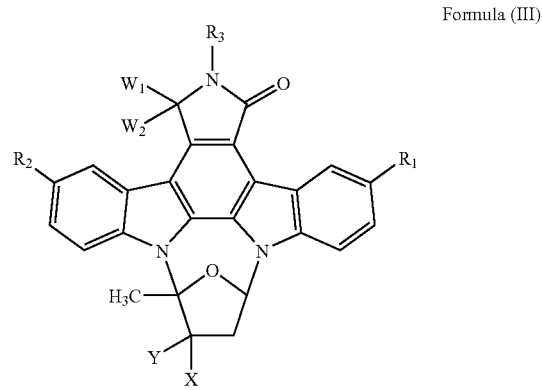

Formula (III)

wherein $R^1$ and $R^2$ are the same or a different residue and are each independently selected from the group consisting of:

a) hydrogen, halogen, substituted or unsubstituted lower alkyl, substituted or unsubstituted lower alkenyl, substituted or unsubstituted lower alkynyl, hydroxy, lower alkoxy, carboxy, lower alcoxycarbonyl, acyl, nitro, carbamoyl, lower alkylaminocarbonyl, —$NR^5R^6$, wherein $R^5$ and $R^6$ are each independently selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, substituted or unsubstituted lower alkylaminocarbonyl, substituted or unsubstituted lower arylaminocarbonyl, alkoxycarbonyl, carbamoyl, acyl or $R^5$ and $R^6$ are combined with a nitrogen atom from a heterocyclic group, b) —$CO(CH_2)_jR^4$, wherein j is 1 to 6, and $R^4$ is selected from the group consisting of
  (i) hydrogen, halogen, —$N_3$,
  —$NR^5R^6$, wherein $R^5$ and $R^6$ are as defined above,
  (iii) —$SR^7$, wherein $R^7$ is selected from the group consisting of hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, —$(CH_2)_aCO_2R^{10}$, (wherein a is 1 or 2, and wherein $R^{10}$ is selected from the group consisting of hydrogen and substituted or unsubstituted lower alkyl), and —$(CH_2)_aCO_2NR^5R^6$, (wherein a and $R^5$ and $R^6$ are as defined above)
  (iv) —$OR^8$, —$OCOR^8$, wherein $R^8$ is selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl c) —$CH(OH)(CH_2)_jR^{4'}$ wherein j and $R^4$ are as defined above;

d) —$(CH_2)_dCHR^{11}CO_2R^{12}$ or —$(CH_2)_dCHR^{11}CONR^5R^6$, wherein d is 0 to 5, $R^{11}$ is hydrogen, —$CONR^5R^6$, or —$CO_2R^{13}$ (wherein $R^{13}$ is hydrogen or a substituted or unsubstituted lower alkyl) and $R^{12}$ is hydrogen or a substituted or unsubstituted lower alkyl;

e) —$(CH_2)_kR^{14}$ wherein k is 2 to 6 and $R^{14}$ is halogen, substituted or unsubstituted aryl, substituted or unsubstituted heteroaryl, —$COOR^{15}$, —$OR^{15}$, (wherein $R^{15}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl or acyl), —$SR^7$ (wherein $R^7$ is as defined above), —$CONR^5R^6$, —$NR^5R^6$ (wherein $R^5$ and $R^6$ are as defined above) or —$N_3$;

f) —$CH=CH(CH_2)_mR^{16}$, wherein m is 0 to 4, and $R^{16}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, —$COOR^{15}$, —$OR^{15}$ (wherein $R^{15}$ is as defined above) —$CONR^5R^6$ or —$NR^5R^6$ (wherein $R^5$ and $R^6$ are as defined above);

g) —$CH=C(CO_2R^{12})_2$; wherein $R^{12}$ is as defined above;

h) —$C\equiv C(CH_2)_nR^{16}$, wherein n is 0 to 4 and $R^{16}$ is as defined above;

i) —$CH_2OR^{22}$, wherein $R^{22}$ is tri-lower alkyl silyl in which the three lower alkyl groups are the same or different or wherein $R^{22}$ has the same meaning as $R^6$.

j) —$CH(SR^{23})_2$ and —$CH_2$—$SR^7$ wherein $R^{23}$ is lower alkyl, lower alkenyl or lower so alkynyl and wherein $R^7$ is as defined above.

$R^3$ is hydrogen, halogen, acyl, carbamoyl, substituted or unsubstituted lower alkyl, substituted or unsubstituted alkenyl, substituted or unsubstituted lower alkynyl or amino;

X represents -$L^1$-X' and Y represents -$L^2$-Y', wherein at least one of X' and Y' is a polymer, either linear or branched, which is bound by $L^1$ and/or $L^2$ to the tetrahydrofuran moiety of the compound of formula (III); $L^1$ and/or $L^2$ are a covalent chemical bond or a linker group which binds the tetrahydrofuran moiety to the polymer X' and/or Y';

when Y' is a polymer, and X' is not a polymer, $L^1$ is a covalent chemical bond and X' is selected from the group consisting of (a) hydrogen, lower hydroxyalkyl, acyl, carboxy, lower alkoxycarbonyl,
(b) —$CONR^{17a}R^{17b}$, wherein $R^{17a}$ and $R^{17b}$ are each independently selected from
  (i) hydrogen, lower alkyl, lower alkenyl, lower alkynyl,
  (ii) —$CH_2R^{18}$; wherein $R^{18}$ is hydroxy, or
  (iii) —$NR^{19}R^{20}$, wherein $R^{19}$ or $R^{20}$ are each independently selected from hydrogen, lower alkyl, lower alkenyl, lower alkynyl or $R^{19}$ or $R^{20}$ are independently the residue of an α-amino acid in which the hydroxy group of the carboxyl group is excluded, or $R^{19}$ or $R^{20}$ are combined with a nitrogen atom to form a heterocyclic group; and
(c) —$CH=N$—$R^{21}$, wherein $R^{21}$ is hydroxy, lower alkoxy, amino, guanidino, or imidazolylamino;

when X' is polymer, and Y' is not a polymer, $L^2$ is a covalent chemical bond and Y' is selected from hydroxy, lower alkoxy, aralkyloxy, or acyloxy;

$W^1$ and $W^2$ are independently hydrogen, hydroxy or $W^1$ and $W^2$ together represent oxygen;

or a pharmaceutically acceptable salt thereof.

The term "lower alkyl", when used alone or in combination with other groups, means a straight chained or branched lower alkyl group containing from 1-6 carbon atoms, preferably from 1-5, more preferably from 1-4 and especially preferably 1-3 or 1-2 carbon atoms. These groups include in particular methyl, ethyl, propyl, isopropyl, butyl, isobutyl, sec-butyl, tert-butyl, pentyl, amyl, isoamyl, neopentyl, 1-ethylpropyl, hexyl, and the like. The lower alkyl moiety of the "lower alkoxy", the "lower alkoxycarbonyl", the "lower alkylaminocarbonyl", "lower hydroxyalkyl" and of the "tri-lower alkylsilyl" groups has the same meaning as "lower alkyl" defined above.

The "lower alkenyl" groups are defined as $C_2$-$C_6$ alkenyl groups which may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like. More preferred $C_2$-$C_6$-alkenyl groups are $C_2$-$C_5$—, $C_2$-$C_4$-alkenyl groups and even more preferably $C_2$-$C_3$-alkenyl groups.

The term "lower alkynyl" groups refers to $C_2$-$C_6$-alkynyl groups which may be straight chained or branched and include ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. More preferred $C_2$-$C_6$-alkynyl groups are $C_2$-$C_5$-, $C_2$-$C_4$-alkynyl groups and even more preferably $C_2$-$C_3$-alkynyl groups.

The term "aryl" group refers to $C_6$-$C_{14}$-aryl groups which contain from 6 up to 14 ring carbon atoms. These groups may be mono-, bi- or tricyclic and are fused rings. The preferred aryl groups include phenyl, biphenyl, naphthyl, anthracenyl, phenanthrenyl and the like. The aryl moiety of the "arylcarbonyl" and the "arylaminocarbonyl" groups has the same meaning as defined above.

The term "heteroaryl" groups may contain 1 to 3 heteroatoms independently selected from nitrogen, sulfur or oxygen and refers $C_3$-$C_{13}$-heteroaryl groups. These groups may be mono-, bi- or tricyclic. The $C_3$-$C_{13}$ heteroaryl groups of the present invention include heteroaromatics and saturated and partially saturated heterocyclic groups. These heterocyclics may be monocyclic, bicyclic, tricyclic. Preferred 5 or 6-membered heterocyclic groups are thienyl, furyl, pyrrolyl, pyridyl, pyranyl, morpholinyl, pyrazinyl, methylpyrrolyl, and pyridazinyl. The $C_3$-$C_{13}$-heteroaryl may be a bicyclic heterocyclic group. Preferred bicyclic heterocyclic groups are benzofuryl, benzothienyl, indolyl, imidazolyl, and pyrimidinyl. The most preferred $C_3$-$C_{13}$-heteroaryls are furyl and pyridyl.

The term "lower alkoxy" includes alkoxy groups containing from 1 to 6 carbon atoms, preferably from 1 to 5, more preferably from 1-4 and especially preferably 1 to 3 or 1 to 2 carbon atoms and may be straight chained or branched. These groups include methoxy, ethoxy, propoxy, butoxy, isopropoxy, tert-butoxy, pentoxy, hexoxy and the like.

The term "acyl" includes lower alkanoyl containing 1 to 6 carbon atoms, preferably from 1 to 5, from 1 to 4, from 1 to 3 or from 1 to 2 carbon atoms and may be straight chained or branched. These groups include preferably formyl, acetyl, propionyl, butyryl, isobutyryl, tertiary butyryl, pentanoyl and hexanoyl. The acyl moiety of the "acyloxy" group has the same meaning as defined above.

The term "halogen" includes fluoro, chloro, bromo, iodio, and the like.

The term "aralkyl" group refers $C_7$-$C_{15}$-aralkyl wherein the alkyl group is substituted by an aryl. The alkyl group and aryl may be selected from the $C_1$-$C_6$ alkyl groups and the $C_6$-$C_{14}$-aryl groups as defined above, wherein the total number of carbon atoms is between 7 and 15. Preferred $C_7$-$C_{15}$-aralkyl groups are benzyl, phenylethyl, phenylpropyl, phenylisopropyl, phenylbutyl, diphenylmethyl, 1,1-diphenylethyl, 1,2-diphenylethyl. The aralkyl moiety of the "aralkyloxy" groups has the same meaning as defined above.

The substituted lower alkyl, alkenyl and alkynyl groups have 1 to 3 independently selected substituents, such as lower alkyl, hydroxy, lower alkoxy, carboxyl, lower alkoxycarbonyl, nitro, halogen, amino, mono- or di-lower alkylamino, dioxolane, dioxane, dithiolane, and dithione. The lower alkyl substituent moiety of the substituted lower alkyl, alkenyl and alkynyl groups, and the lower alkyl moiety of the lower alkoxy, the lower alkoxycarbonyl, and the mono- or di-lower alkylamino substituents of the substituted lower alkyl, alkenyl and alkynyl groups have the same meaning as "lower alkyl" defined above.

The substituted aryl, the substituted heteroaryl and the substituted aralkyl groups each has 1 to 3 independently selected substituents, such as lower alkyl, hydroxy, lower alkoxy, carboxyl, lower alkoxycarbonyl, nitro, amino, mono- or di-lower alkylamino, and halogen. The lower alkyl moiety of the lower alkyl, the lower alkoxy, the lower alkoxycarbonyl, and the mono- or di-lower alkylamino groups among the substituents has the same meaning as lower alkyl defined above.

The heterocyclic group formed by $R^5$ and $R^6$ combined with a nitrogen atom includes pyrrolidinyl, piperidinyl, piperidino, morpholinyl, morpholino, thiomorpholino, N-methylpiperazinyl, indolyl, and isoindolyl.

The α-amino acid groups include glycine, alanine, proline, glutamic acid and lysine, which may be in the L-form, the D-form or in the form of a racemate.

Preferably, $R^1$ and $R^2$ are independently selected from the group consisting of hydrogen, halogen, nitro, —$CH_2OH$, —$(CH_2)_k R^{14}$, —CH=CH$(CH_2)_m R^{16}$, —C≡C$(CH_2)_n R^{15}$, —CO$(CH_2)_j R^4$ wherein $R^4$ is —$SR^7$, $CH_2O$— (substituted or unsubstituted) lower alkyl (wherein the substituted lower alkyl is preferably methoxymethyl. methoxyethyl os ethoxymethyl), —$NR^5 R^6$.

In the above preferred meanings of $R^1$ and $R^2$, the residue $R^{14}$ is preferably selected from phenyl, pyridyl, imidazolyl, thiazolyl, tetrazolyl, —$COOR^{15}$, —$OR^{15}$ (wherein $R^{15}$ is preferably selected from hydrogen, methyl, ethyl, phenyl or acyl), —$SR^7$ (wherein $R^7$ is preferably selected from substituted or unsubstituted lower alkyl, 2-thiazoline and pyridyl) and —$NR^5 R^6$ (wherein $R^5$ and $R^6$ are preferably selected from hydrogen, methyl, ethyl, phenyl, carbamoyl and lower alkylaminocarbonyl). Moreover the residue $R^{16}$ is preferably selected form hydrogen, methyl, ethyl, phenyl, imidazole, thiazole, tetrazole, —$COOR^{15}$, —$OR^{15}$ and —$NR^5 R^6$ (wherein the residues $R^{15}$, $R^5$ and $R^6$ have the preferred meanings as described above). In the above preferred meanings of $R^1$ and $R^2$, the residue $R^7$ is preferably selected from the group consisting of substituted or unsubstituted lower alkyl, substituted or unsubstituted phenyl, pyridyl, pyrimidinyl, thiazole and tetrazole. Further k is preferably 2, 3 or 4, j is preferably 1 or 2 and m and n are independently preferably 0 or 1.

Preferably $R^3$ is hydrogen or acetyl, most preferably hydrogen.

Preferably, each $W^1$ and $W^2$ is hydrogen.

When Y' is a polymer, and X' is not a polymer, X' is preferably selected from carboxy, hydroxymethyl or a lower alkoxycarbonyl, with methoxycarbonyl and carboxyl being particularly preferred.

When X' is polymer, and Y' is not a polymer, Y' is preferably selected from hydroxy or acetyloxy, most preferred hydroxy.

A very preferred embodiment of the present invention refers to the compound K252-a conjugated in the position X and/or Y to a polymer. Therefore, in a very preferred embodiment of the present invention, the polymer conjugate of formula (III) is represented by a compound wherein $R_1$, $R_2$, $R_3$, $W_1$, and $W_2$ are hydrogen and at least one of X' and Y' is a polymer, whereby if Y' is a polymer, and X' is not a polymer, X' is methoxycarbonyl, and if X' is a polymer, and Y' is not a polymer, Y' is hydroxy.

A very preferred embodiment of the present invention refers to the compound K252-b conjugated in the position X and/or Y to a polymer. Therefore, in a very preferred embodiment of the present invention, the polymer conjugate of formula (III) is represented by a compound wherein $R_1$, $R_2$, $R_3$, $W_1$, and $W_2$ are hydrogen and at least one of X' and Y' is a polymer, whereby if Y' is a polymer, and X' is not a polymer, X' is carboxyl, and if X' is a polymer, and Y' is not a polymer, Y' is hydroxy.

The compounds of the present invention may be prepared as pharmaceutically acceptable salts including salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, glycolic, gluconic, succinic, aryl sulfonic, (e.g., p-toluene sulfonic acids, benzenesulfonic), phosphoric, malonic, and the like. Suitable acids for formation of pharmaceutically acceptable salts are known to a person skilled in the art. Furthermore, pharmaceutically acceptable salts of compounds of the present invention may be formed with a pharmaceutically acceptable cation. Pharmaceutically acceptable cations are known to a person skilled in the art and include alkali cations (Li+, Na+, K+), earth alkali cations (Mg2+, Ca2+, Ba2+), ammonium and organic cations, such as quaternary ammonium cations.

The polymer moiety according to the present invention, which, for example, is represented in the general formula (III) by X' and/or Y', has to be biocompatible, can be of natural or semi-synthetic or synthetic origin and can have a linear or branched structure. Exemplary polymers include without limitation polyalkylene glycols, polyalkylene oxides, polyacrylic acid, polyacrylates, polyacrylamide or N-alkyl derivatives thereof, polymethacrylic acid, polymethacrylates, polyethylacrylic acid, polyethylacrylates, polyvinylpyrrolidone, poly(vinylalcohol), polyglycolic acid, polylactic acid, poly(lactic-co-glycolic) acid, dextran, chitosan, polyaminoacids.

In a very preferred embodiment of the present invention, the polymer is polyethylene glycol (PEG) group, wherein the terminal OH group can optionally so be modified e.g. with $C_1$-$C_5$ alkyl or $C_1$-$C_5$ acyl groups, preferably with $C_1$—, $C_2$- or $C_3$-alkyl groups or $C_1$—, $C_2$— or $C_3$ groups. Preferably, the modified polyethylene glycol is methoxy-polyethyleneglycol (mPEG).

The polymer used according to the present invention has a molecular weight ranking from 100 to 100,000 Da, preferably from 200 to 50,000 Da, and more preferably from 500 to 10,000 Da. According to one preferred aspect of the invention, the polymer is a short-chain PEG which preferably has a terminal OH and/or methoxy group with a molecular weight ranking from 200 to 1500 Da, preferably from 400 to 1200 Da and even more preferably from 550 to 1100. In the most preferred embodiment, the short-chain PEG has an average molecular weight of 550 Da or of 1100 Da. According to a second preferred aspect of the invention, the polymer is a long-chain PEG which preferably has a terminal OH and/or methoxy group, with a molecular weight ranking from 4,000 to 6,000 Da, and preferably from 4,500 to 5,500 Da. In the most preferred embodiment of this aspect of the invention, a long-chain PEG or mPEG with an average molecular weight of 2,000 Da or of 5,000 Da is used.

The polymer chain of the polymer conjugate of formulae (I), (II) and/or (III) is conjugated by a covalent chemical bond to the active agent in order to provide a stable conjugate. FIG. 1a and FIG. 1b show e.g. the preferred polymer conjugate of formula (III). The polymer can be bound directly to the compound of formulae (I) or (II) or to the K-252a derivative of formula (III). In this case of formula (III), $L^1$ and $L^2$ are a covalent bond.

In a preferred embodiment of the present invention, the polymer moiety are bound to the indolocarbazole derivative by using a linker group. In the preferred embodiment of the compound of formula (III), the polymer moiety X' and/or Y' are bound by a linker group, whereby in this embodiment, $L^1$ and $L^2$ represent the linker group. In the preferred embodiment of formula (III) of the present invention, the term linker group $L^1$ and/or $L^2$ means a group which is obtained by the chemical reaction of the residue on the C3 position of the tetrahydrofuran moiety of the formula (III) and the reactive group on the polymer moiety. Therefore, $L^1$ and $L^2$, which couple the polymer moieties X' and Y' to the tetrahydrofuran ring, may represent a linker group as defined above.

The linker group can be any residue known to those skilled in the art of polymer conjugation, obtained by the reaction of the functional group suitable for conjugation on the indolocarbazole compounds of formulae (I) or (II), preferably on the cyclic moiety $R^c$ and/or $R^d$, or on the substituent on the tetrahydrofuran ring of formula (III) and the polymer or the polymer activated by a reactive group. Exemplary linker group, e.g. exemplary $L^1$ and/or $L^2$ groups, include without limitation ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide bonds. Preferably, the linker groups or in particular $L^1$ and $L^2$ are selected from a carbamate, an ether, an ester, a carbon, an amide and/or an amine bond.

Moreover, the linker group may optionally contain one or more spacer groups. In the context of the present invention, a spacer group is defined as a bifunctional group, having on both termini a reactive functional end-group. With the one reactive end-group, the spacer reacts with the polymer moiety, e.g. X' and Y', or with the reactive group on the polymer moiety. With the further functional group on the other terminus, the spacer group binds to the functional group suitable for conjugation on the indolocarbazole compounds of formulae (I) or (II), preferably on the cyclic moiety $R^c$ and/or $R^d$, or to the tetrahydrofuran ring of formula (III), preferably with the residue on the C3 position of the tetrahydrofuran ring of formula (III). Suitable spacer groups are known to those skilled in the art. Examples of spacer groups include, but are not limited to hetero-, bi-functional small molecules or polymer. For example, the spacer group may be represented by bifunctional $C_6$-$C_{12}$ alkyl groups or heterobifunctional alkyl groups containing from 1-3 heteroatoms selected from N, S and O or an intermediary short bifunctional PEG chain.

In a most preferred embodiment, the polymer, represented in the general formula (III) by X' or Y', preferably covalently binds directly or by a spacer group to an oxygen atom derived from the hydroxy group on the C3 position of the tetrahydrofuran moiety of the K-252a derivative. In this preferred embodiment, in the general formula (III), Y' represents the polymer moiety and $L^2$ is preferably a carbamate or an ether bond (FIG. 1a). In an alternative most preferred embodiment, the polymer is covalently conjugated directly or by a spacer group to an carbonyl group derived from the methylester group on the C3 position of the tetrahydrofuran moiety of the K-252a derivative. In this alternative embodiment, in the general formula (III), X' represents the polymer moiety and L' is preferably an amide or amine bond (FIG. 1b).

The covalent attachment of the polymer moiety to the indolocarbazole compounds of formulae (I), (II), or (III) is obtained by known chemical synthesis. In particular, covalent attachment of the polymer to K-252a or its derivatives to obtain the compounds of formula (III) may be accomplished by known chemical synthesis techniques. For example, in one exemplary embodiment of the present invention, the polymer conjugation of K-252a or its derivatives can be accomplished by reacting an isocyanate-activated polymer with K-252a or its derivatives under suitable reaction conditions as generally depicted by the following reaction scheme:

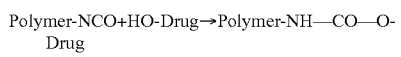
Polymer-NCO+HO-Drug→Polymer-NH—CO—O-Drug

According to this synthesis scheme, FIG. 2 shows an example of the present invention, wherein a compound of formula (III) is obtained by the reaction of the polymer moiety Y' which is an isocyanate-activated PEG and the hydroxy group on the C3 position of the tetrahydrofuran moiety of K-252a. The conjugation between polymer and K-252a is hence obtained by the linker group $L^2$ which is a carbamate linker group.

In the present invention, it was surprisingly found that compared to members of indolocarbazole compounds and in particular to K-252a or its derivatives, the compounds of formula (I), (II) and/or (III) exhibit an improved pharmacokinetic and toxicologic performance due to their increased solubility, leading to an improved bioavailability. In another aspect of the present invention, it was surprisingly found that the compounds of formulae (I), (II) and/or (III) show a limited systemic absorption upon topical administration due to their increased molecular size and hydrophilicity, thus reducing the systemic toxicity and/or side-effects (see Example 2).

It has further been surprisingly found by the inventors of the present application that the K-252a polymer conjugates of formulae (I), (II) and/or (III) exhibit a significant increase in selectivity in the inhibitory activity against TrkA tyrosine kinase in comparison with the non-selective kinase inhibitory activity of the indolocarbazole compounds itself and in particular of K-252a and its derivatives (see Example 3). Thus, the conjugation of an indolocarbazole compound and in particular of K-252a to a polymer molecule according to the invention leads to the provision of an active agent selective with regard to its therapeutic target with the consequent decrease of undesired side effects.

Hence a further aspect of the present invention is the use of compounds of formulae (I), (II) and (or III) as active agents in a medicament. In a preferred aspect of the invention, the compounds of formula (I), (II) and/or (III) are used as active agents in a medicament for systemic administration and treatment. In a further preferred aspect, the invention relates to the use of compounds of formula (I), (II), and/or (III) as active agents in a topical medicament.

In particular the conjugated polymer compounds of the present invention are used as active agents in a medicament useful for the prevention, alleviation and treatment of HMGB1-associated pathologies.

An HMGB1-associated pathology is a condition in a patient wherein an increased concentration of the nuclear protein HMGB1 and/or of HMGB1 homologous proteins in the acetylated or non-acetylated form is present in the biological fluids and tissues, compared to the concentration in normal subjects where these HMGB1 nuclear proteins are practically undetectable. The extracellular HMGB1s, act as potent chemotactic pro-inflammatory chemokines. The HMGB1-associated pathologies are hence pathologies with a strong inflammatory basis, pathologies which result from the stimulation of cytokine such as TNF-alpha, IL-1, IL-6 etc., or pathologies which result from toxic events such as intoxication, infection, burn, etc. In particular, high concentrations of the HMGB1 protein and homologous proteins have been found and determined in plasma of patients with sepsis, in plasma and synovial fluid of rheumatoid arthritis patients, in brains of Alzheimer's disease patients, in plasma and tissues of melanoma patients, in plasma of systemic lupus erythematosus patients, in atherosclerotic plaques of atherosclerotic patients, etc. The determination and evidence of HMGB1 protein and/or homologous proteins in biological fluids and tissues may be detected by common diagnostic tools known by the skilled person in the art, including, for example, detection by ELISA assays etc.

Therefore, a variety of diseases are characterized by the relevant presence of extracellular HMGB1, which in particular include but are not limited to inflammatory diseases, stenosis, restenosis, atherosclerosis, rheumatoid arthritis, autoimmune diseases, tumors, infective diseases, sepsis, acute inflammatory lung injury, lupus erythematosus, neurodegenerative diseases, diseases of the central and peripheral nervous system and multiple sclerosis. In an especially preferred embodiment, the conjugated polymer compounds of formulae (I), (II) and/or (III) are used for the prevention, alleviation and treatment of cardiovascular diseases, particularly atherosclerosis and/or restenosis occurring during or after angioplasty. More preferably, the medicament is used for blocking, retarding and/or impairing connective tissue regeneration in restenosis during or after angioplasty.

In a particularly preferred aspect of the invention, the conjugated polymer compounds of formulae (I), (II) and/or (III) are efficient for the use as active agent in a medicament for the prevention, alleviation and treatment of neurological disorders, neuropathies and neurodegenerative disorders of the central and peripheral nervous system.

It was further shown by the inventors that the new polymer conjugate compounds are able to reduce and/or inhibit the plasma cytokine secretion by systemic treatment. Therefore, the polymer conjugate compounds are used as active agents in a medicament for systemic administration useful for the prevention, alleviation and/or treatment of pathologies in which an increase of plasma cytokine secretion is involved. These pathologies are preferably pathologies, in which a secretion of TNF-α, IFN-γ, MCP-1, MIP-1 and/or RANTES are mainly involved.

In particular, in the context of the present invention, pathologies which are associated with an increased plasma cytokine secretion include but are not limited to inflammatory diseases, autoimmune diseases, systemic inflammatory response syndrome, reperfusion injury after organ transplantation, cardiovascular affections, obstetric and gynecologic diseases, infectious diseases, allergic and atopic diseases, solid and liquid tumor pathologies, transplant rejection diseases, congenital diseases, dermatological diseases, neurological diseases, cachexia, renal diseases, iatrogenic intoxication conditions, metabolic and idiopathic diseases, and ophthalmological diseases.

In a most preferred embodiment, the compounds of the invention are used as active agents in a medicament for systemic treatment useful for the prevention, alleviation and/or treatment of Behçet's disease, Sjögren's syndrome, vasculitis, uveitis, retinopathies.

In yet another particular aspect of the invention, it is preferred that the conjugated polymer compounds of the present invention are used as active agents in a topical medicament useful for the prevention, alleviation and/or treatment of dermal pathologies.

The dermal pathologies preferred in the context of the present invention are pathologies characterized by hyperproliferation of the keratinocytes, such as psoriasis, atopic dermatitis, chronic eczema, acne, pitiriasis rubra pilaris, keloids, hypertrophic scars and skin tumors, such as keratoacanthoma, squamous cell carcinoma, basal cell carcinoma. In a more preferred embodiment, the compounds of the present invention are used as active agents in a topical medicament useful for the prevention, alleviation and treatment of psoriasis.

Due to the increased selectivity of the compounds of the invention in the inhibition of TrkA, a further aspect of the invention is the use of said conjugated compounds in the prevention, alleviation and treatment of pathologies in which TrkA plays a crucial role in the pathophysiological mechanism, which leads to the development of the pathologies. In this context, in a very preferred embodiment of the invention, the conjugated K-252a polymer compounds of formulae (I), (II), and/or (III) are used as active agent in a medicament for the prevention, alleviation and treatment of NGF-related pain and hyperalgesia.

Hence a further aspect of the present invention is the use of a compound of formulae (I), (II), and/or (III) optionally as defined above for the manufacture of a medicament for the prevention, alleviation or/and treatment of pathologies as defined above.

The compounds of formulae (I), (II), and/or (III) may be used either alone or in combination with one or several further active agents. In particular, the polymer conjugate compounds of the invention may be used in combination with at least one further agent capable of inhibiting an early mediator of the inflammatory cytokine cascade, e.g. an antagonist or inhibitor of a cytokine selected from the group consisting of TNF, IL-1α, IL-1β, IL-R$_a$, IL-8, MIP-1α, MIF-1β, MIP-2, MIF and IL-6.

Further agents which can be used in combination with the polymer compounds of the invention are e.g. antagonists and/or inhibitors of RAGE, antagonists and/or inhibitors of HMGB1, antagonists and/or inhibitors of the interaction of a Toll-like receptor (TCR) with HMGB1, the functional N-terminal lectin-like domain (D1) of thrombomodulin and/or a synthetic double-stranded nucleic acid or nucleic acid analogue molecule with a bent shape structure as described in the international patent application WO 2006/002971.

The compound of formulae (I), (II), and/or (III) or a pharmaceutically acceptable salts thereof can be administered as they are, or in the form of various pharmaceutical compositions according to the pharmacological activity and the purpose of administration. Yet another aspect of the present invention is a pharmaceutical composition comprising an effective amount of at least one compound of formulae (I), (II), and/or (III) optionally together with pharmaceutically acceptable carriers, adjuvants, diluents or/and additives. Pharmaceutical carriers, adjuvants, diluents or/and additives are known to a person skilled in the art and may therefore be applied in the formulation of the pharmaceutical composition comprising a compound of the present invention.

The pharmaceutical composition of the present invention may be administered in a convenient manner known by a person skilled in the art, e.g. by a physician. In particular, the pharmaceutical composition of the invention may be administered by injection or infusion, in particular by intravenous, intramuscular, transmucosal, subcutaneous or intraperitoneal injection or infusion and/or by oral, topical, dermal, nasal, inhalation, aerosol and/or rectal application, etc. The administration may be local or systemic. Preferably, the administration of the compound and the pharmaceutical composition of the invention may be made by parenteral administration, particularly in the form of liquid solutions or suspensions; or oral administration, particularly in the form of tablets or capsules, or intranasally, particularly in the form of powders, nasal drops, or aerosols; or dermally, via, for example, ointments, cremes, oils, liposomes or trans-dermal patches.

According to one aspect of the invention, the pharmaceutical composition is administered systemically. In particular, the polymer conjugate compounds can be administered by injection or infusion, in particular by intravenous, intramuscular, transmucosal, subcutaneous or intraperitoneal injection or infusion and/or by oral administration.

In a still most preferred embodiment, the pharmaceutical composition of the present invention are administered by topical application, in particular by dermal application. In case of a dermal application the administration of the compounds of the present invention may be made in the form of liposomes.

In a further most preferred embodiment of the invention, the pharmaceutical composition are administered reversibly immobilized on the surface of a medical device, in particular by binding, coating and/or embedding the compound and composition of the invention an a medical device, such as but not limited to, stents, catheters, surgical instruments, cannulae, cardiac valves, or vascular prostheses. After contacting the medical device with body fluid or body tissue, the reversibly immobilised compounds are liberated. Consequently, the coated medical devices act as drug delivery devices eluting the medicament, whereby the drug delivery kinetics can be controlled, providing an immediate release or a controlled, delayed or sustained drug delivery, for example. Coating technologies of medical devices are well known to the person skilled in the art.

The pharmaceutical composition of the present invention may be used for diagnostic or for therapeutic applications. For diagnostic applications, the compound of formula (I), (II), and/or (III) may be present in a labelled form, e.g. in a form containing an isotope, e.g. a radioactive isotope or an isotope which may be detected by nuclear magnetic resonance. A preferred therapeutic application is, in the case of a topical application, the prevention, alleviation and treatment of psoriasis, while in the case of a systemic application, the prevention, alleviation and treatment of connective tissue regeneration in restenosis.

The compounds of this invention can be employed as the sole active agent in a pharmaceutical composition. Alternatively, they can be used in combination with other active ingredients, e.g. other active pharmaceutical ingredients in the treatment of the above defined pathologies.

The concentrations of the compounds of this invention in the pharmaceutic composition can vary. The concentration will depend upon factors such as the total dosage of the drug to be administered, the chemical characteristics (e.g., hydrophobicity) of the compounds employed, the route of administration, the age, body weight and symptoms of a patient. The compounds of this invention typically are provided in an aqueous physiological buffer solution containing about 0.1 to 10% w/v compound for parenteral administration. Typical dose ranges are from about 1 µg to about 1 g/kg of body weight per day; a preferred dose range is from about 0.01 mg/kg to 100 mg/kg of body weight per day, and preferably about 0.1 to 20 mg/kg once to four times per day. A preferred dosage of the drug to be administered is likely to depend on variables such as the type and extent of the progression of the disease or disorder, the overall health status of the particular patient, the relative biological efficacy of the selected compound and the formulation of the compound excipient, and its route of administration.

A still further aspect of the invention is the use of the non-conjugated K-252a compound or a derivative thereof for the manufacture of a medicament for the prevention, alleviation and/or treatment of Behcet's disease.

Preferred K-252a derivatives include synthetic and/or chemically modified compounds, e.g. compounds having substituents on the ring system, e.g. $C_1$-$C_4$ alkyl groups, compounds wherein the methyl ester group has been replaced by another ester group, an amide group or by H or a cation and/or compounds, wherein the N-atom in the cyclic amide group is substituted with a $C_1$-$C_4$ alkyl group.

The present invention is further illustrated by the following figures and examples.

FIG. 4a shows the results of the average plasma concentration of K-252a detected in mice plasma fraction after topical administration of K-252a.

FIG. 4b is a graph showing the profile of mean plasma concentration versus time after a single dermal administration at a dosage of about 10 µmol/kg, corresponding to 5.07 mg/kg, of K-252a.

Figure 6:
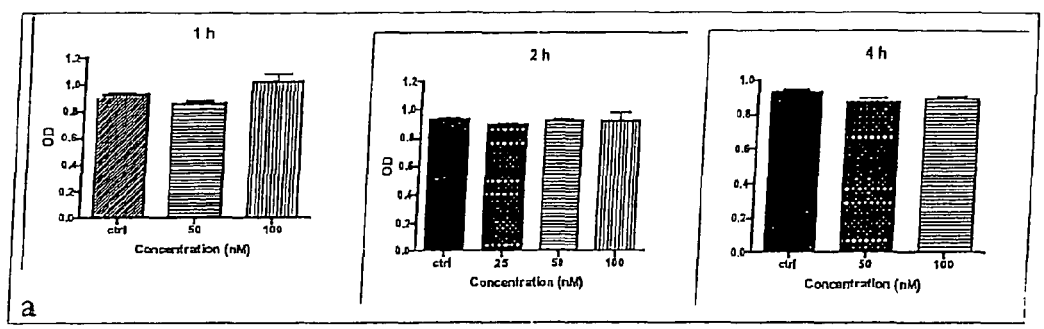
Figure 6:
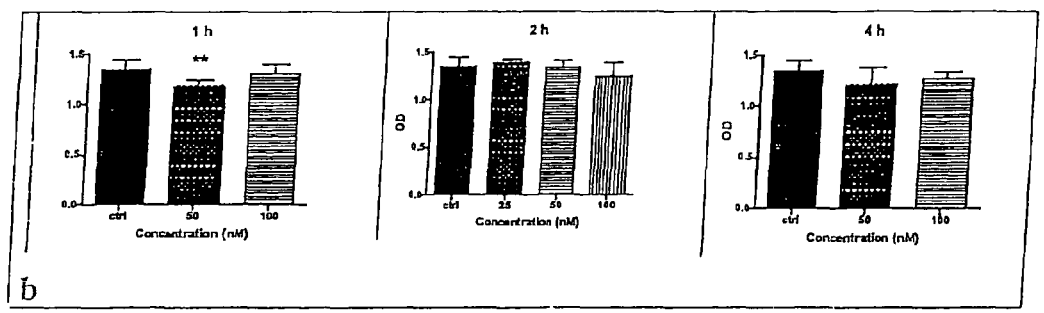

FIG. 6 shows the antiproliferative activity on keratinocyte of K252a-PEG(2K) in the MTT assay. FIG. 6a refers respectively to 1, 2 and 4 hours of contact period with the cellular counting being performed after 48 h. FIG. 6b refers respectively to 1, 2 and 4 h of contact period with the cellular counting being performed after 96 h.

Figure 7:
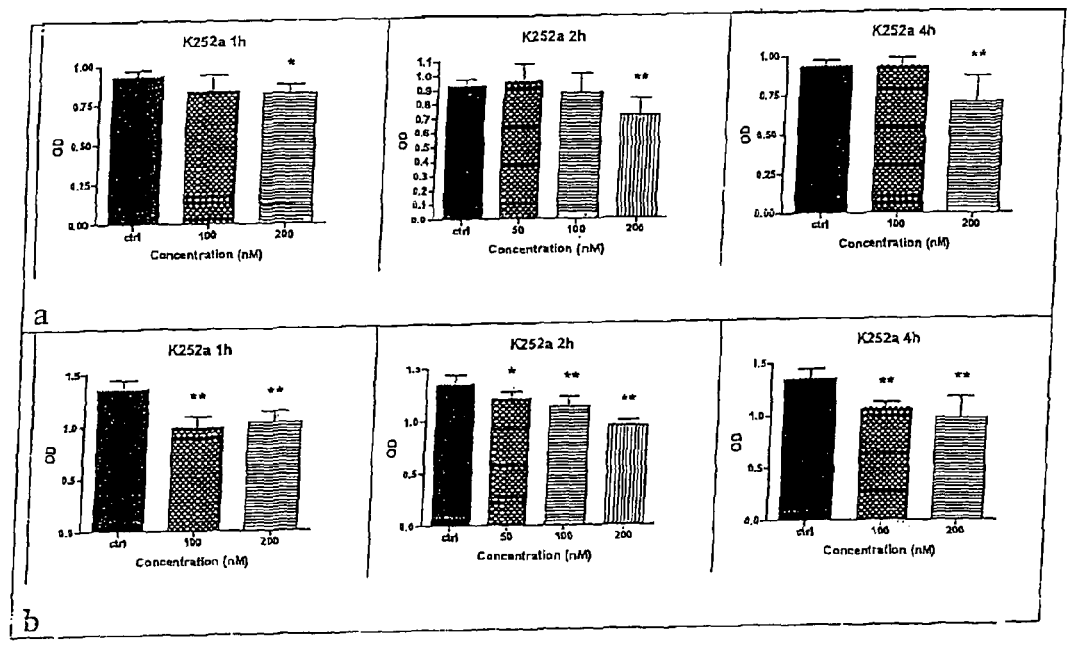

FIG. 7 shows the antiproliferative activity on keratinocyte of K252a in the MTT assay. FIG. 7a refers respectively to 1, 2 and 4 hours of contact period with the cellular counting being performed after 48 h. FIG. 7b refers respectively to 1, 2 and 4 h of contact period with the cellular counting being performed after 96 h.

Figure 8:
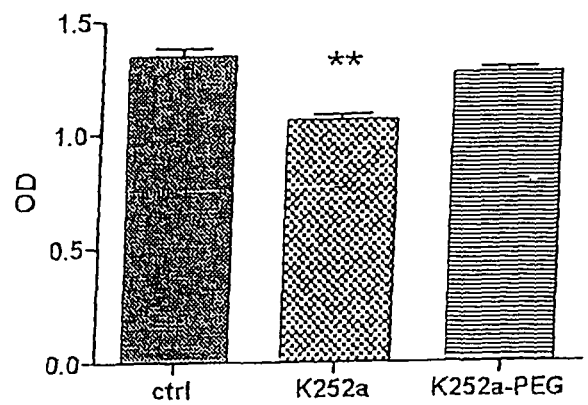

FIG. 8 is a graph comparing the antiproliferative activity on keratinocyte in the MTT assay of K252a and K252a-PEG (2K) after 4 h of contact period and after having performed the cellular counting after 96 h.

FIG. 9a and FIG. 9b report the inhibiting activity of K-252a and K-252a-PEG (2K), respectively, against common tyrosine kinases.

Figure 10:
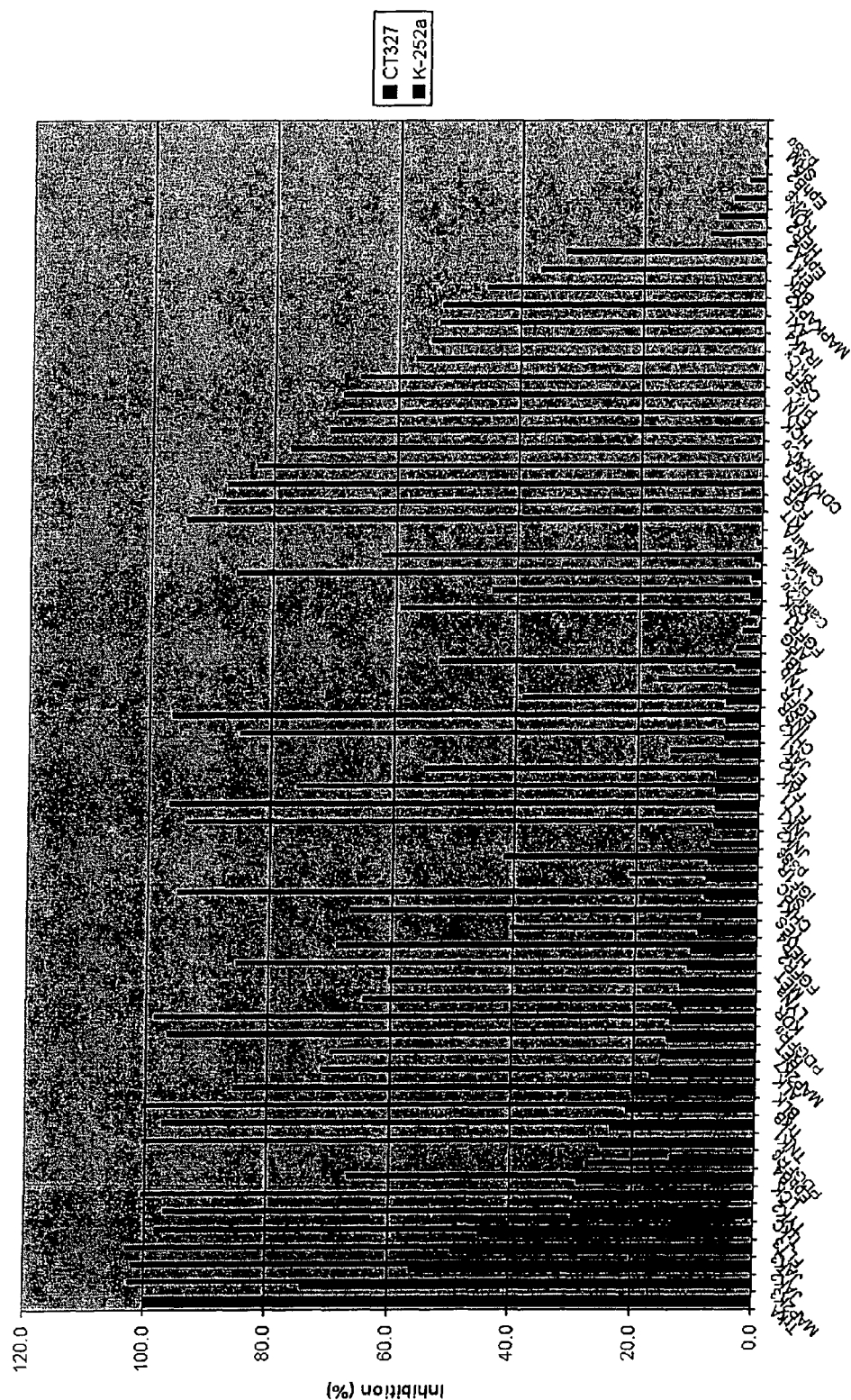

FIG. 10 is a graph showing the kinase inhibition profiles for K-252a and K-252a-PEG(2K), respectively, and reporting the comparison of the selectivity in kinase inhibition of K-252a-PEG(2k) versus K-252a. The data reported in FIG. 10 are normalized with respect to the TrkA inhibition activity.

Figure 11:
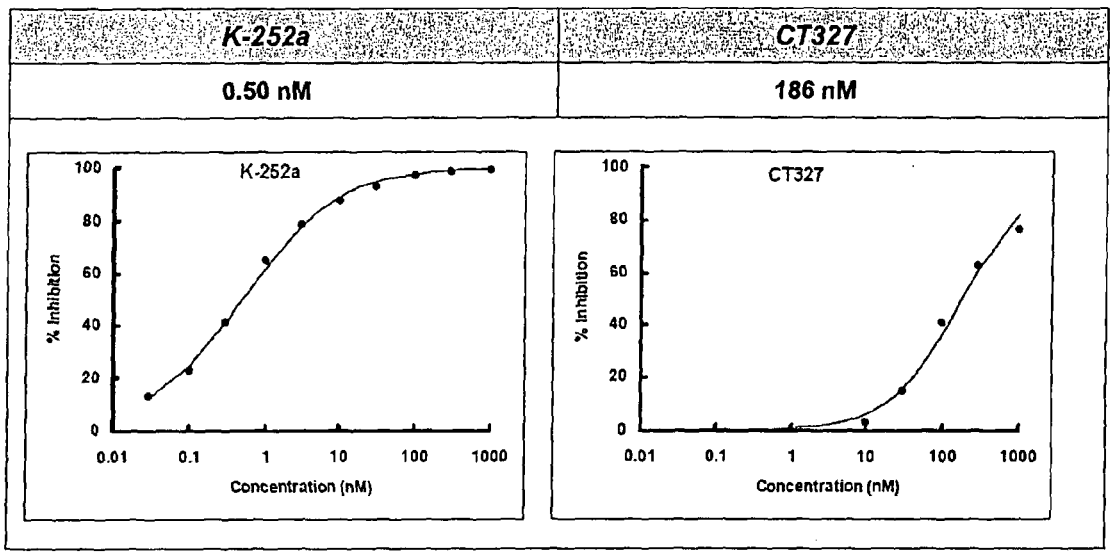

FIG. 11 shows the $IC_{50}$ of K-252a and K-252a-PEG(2K) against TrkA and the respective inhibition curve.

Figure 12:
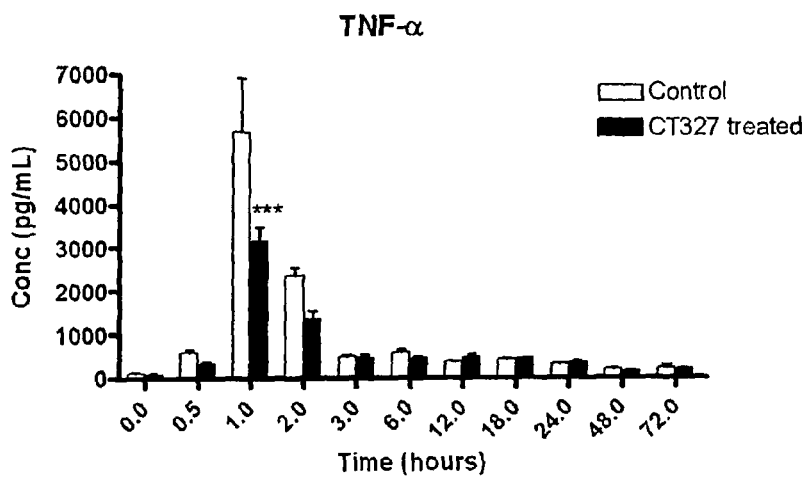

FIG. 12 shows the TNF-α secretion inhibition in the plasma of mice treated with K-252a-PEG(2K) before inducing endotoxemia with an LPS-dose injection in comparison to control mice which received only a vehicle solution before LPS treatment In the Figure, error bars represent SEM—Data analyzed by two-way ANOVA followed by Bonferroni post-tests.

Figure 13A:
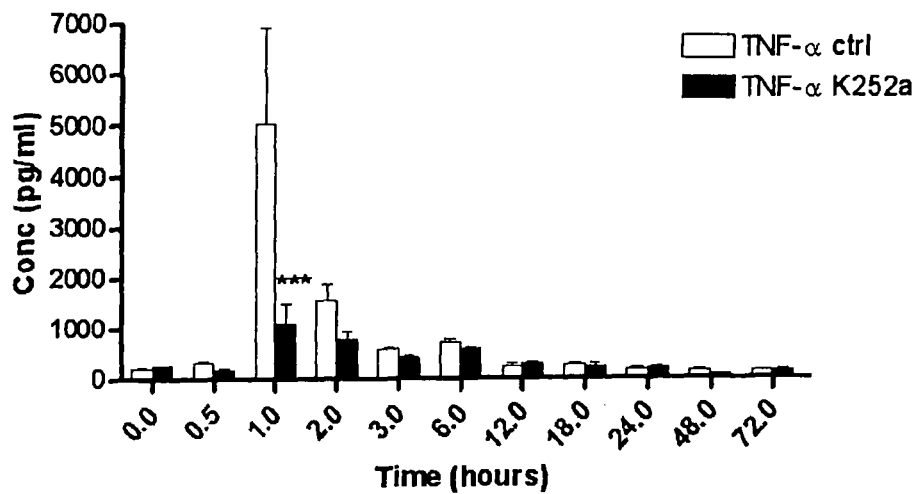
Figure 13B:
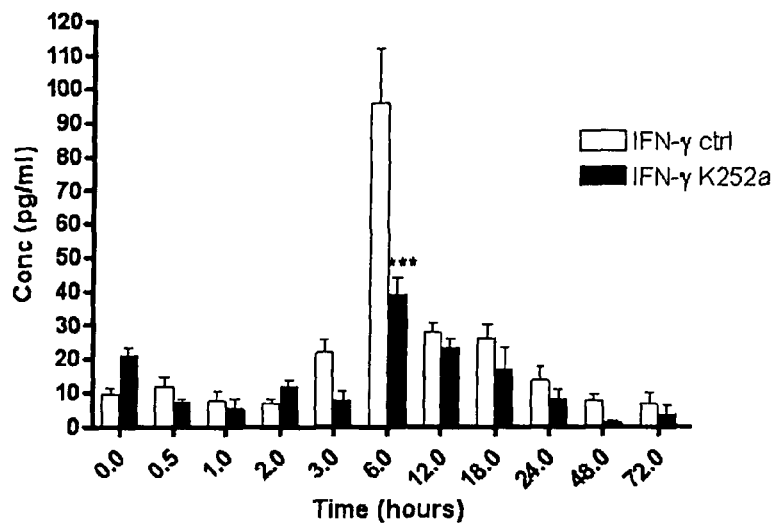
Figure 13C:
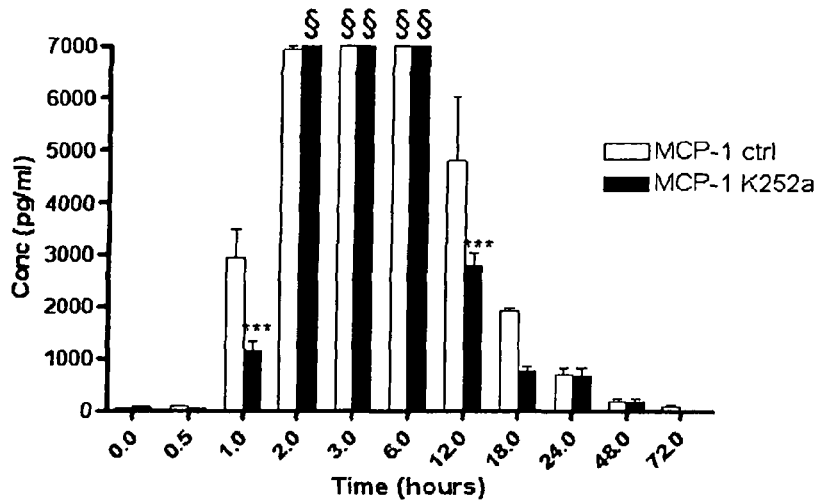
Figure 13D:
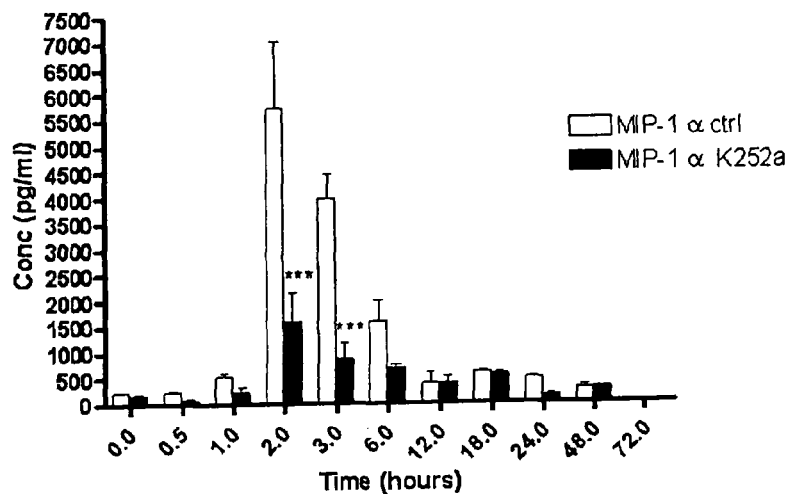
Figure 13E:
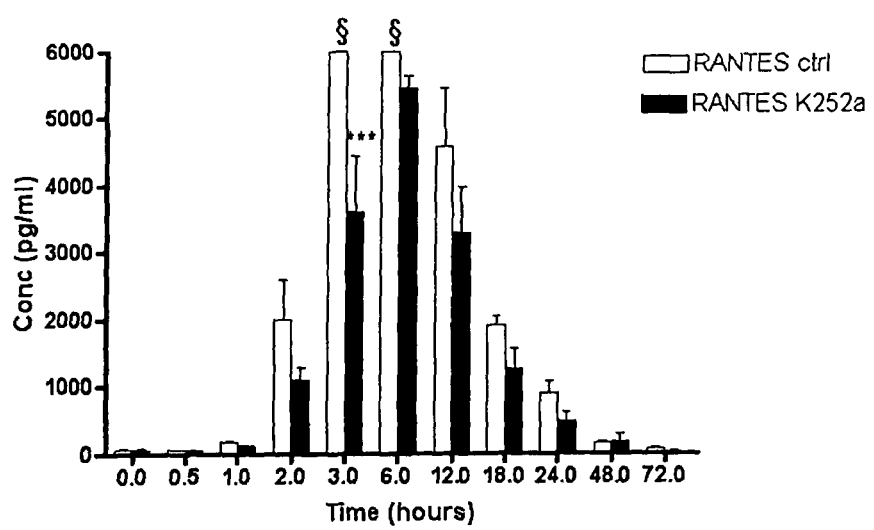

FIGS. 13a) to 13e) show the TNF-α, IFN-γ, MCP-1, MIP-1 and RANTES secretion inhibition, respectively, in plasma of mice treated with non-conjugated K-252a before inducing endotoxemia with an LPS dose injection in comparison to control mice which received only a vehicle solution before LPS treatment. In the figures, the sign "§" stands for out of range results.

EXAMPLES

In the following examples, the product identified with the terms "K-252a-PEG", "K-252a-PEG(2K)" or "CT327" corresponds to a compound according to the present invention wherein K-252a is conjugated to the —OH group of the tetrahydrofuran moiety with a linear 2 kDa PEG chain by a carbamate bond.

Example 1

Synthesis of a K-252a-PEG(2K) Conjugate (Compound CT327)

Figure 1A:
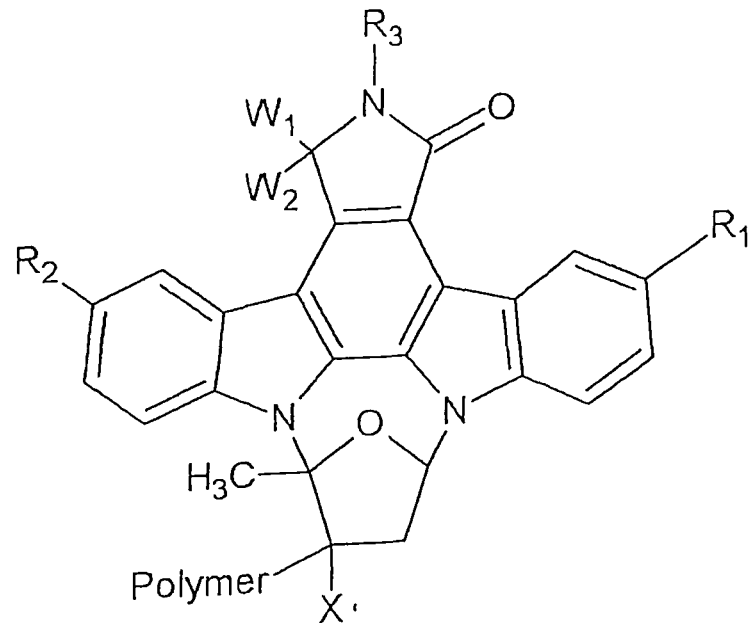
FIGS. 1a and 1b depict the structure of the polymer conjugates of K-252a and derivatives thereof.
Figure 1B:
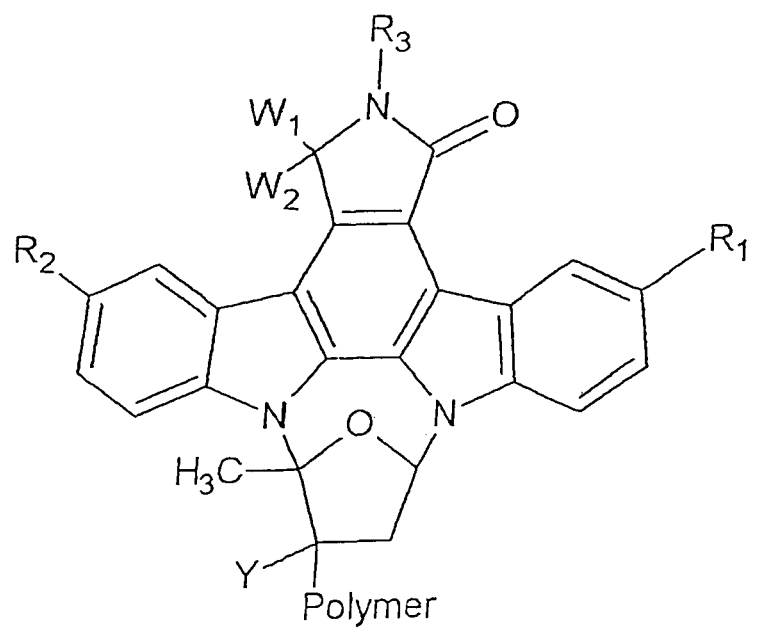
Figure 2:
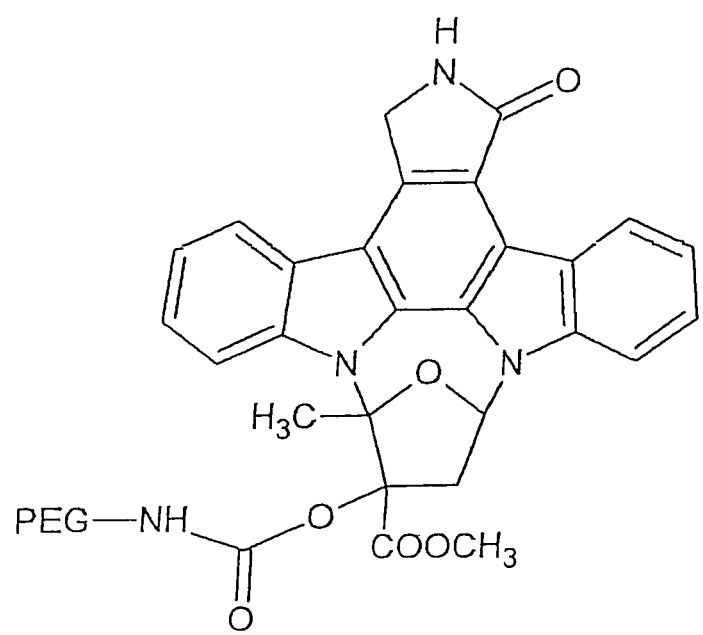
FIG. 2 depicts the structure of a K-252a-PEG conjugate where PEG is linked to drug by carbamate bond.
Figure 3:
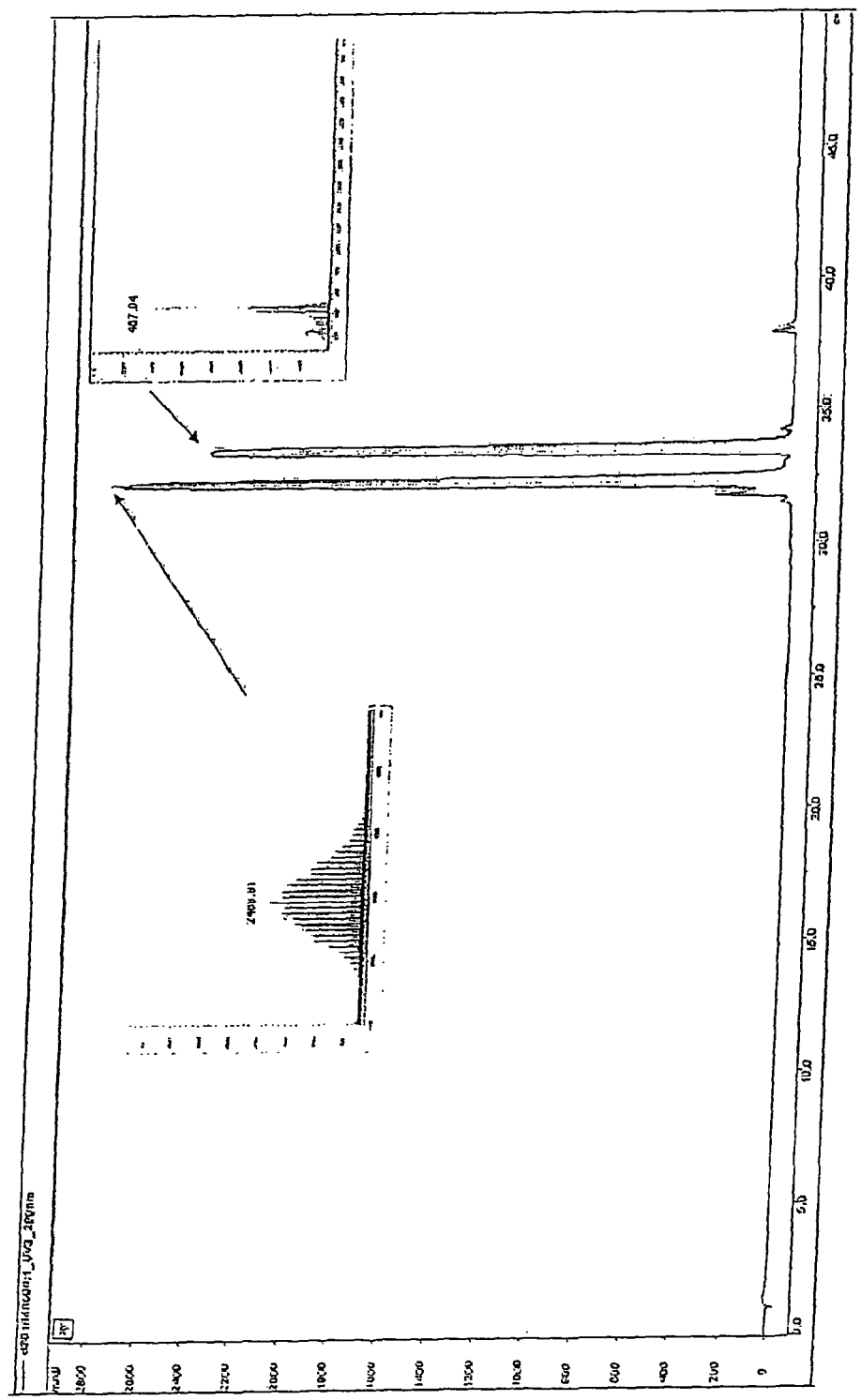
FIG. 3 is a chromatogram of the purification of a PEG conjugate wherein PEG is linked to K-252a by carbamate linkage and the PEG chain has an average molecular weight of 2000 Da. In the Inserts, the MALDI-TOF spectra of the main peaks is shown.

A 1 mg/mL solution of K-252a in dichloromethane was prepared dissolving 1.5 mg of K-252a (corresponding to 3.208 μmol) in 1.5 mL of $CH_2Cl_2$ by gentle stirring. The solution was added into a glass flask containing 65.05 mg (32.525 μmol) of methoxy-PEG-isocyanate 2K (m-PEG-isocyanate with an average molecular weight of 2000 Da) and 100 μL of a 32.684 mg/mL triethylamine solution in $CH_2Cl_2$ as basic catalyst. Both the polymer and the catalyst were used in a 10-fold molar ratio compared to K-252a. The mixture was kept at room temperature under magnetic stirring (spin rate about 500 rpm) and gentle nitrogen flux overnight (reaction time=16 h 40'). The solution was then evaporated and the solid residue was treated with 300 μL of DMSO. The mixture was purified by RP-HPLC on a C18 column in order to obtain the desired product (peak corresponding to about 59/41 ACN/water gradient). The corresponding fractions of four subsequent purification processes were pooled and dried by ACN evaporation and then freeze-dried. A MALDI-TOF analysis confirmed the identification of the product with K-252a-PEG conjugate (polydisperse mass peak with a maximum m/z value of 2468.81) [FIG. 2,3].

Example 2

In Vivo Pharmacokinetic Studies

Example 2.1

Dermal Absorption Study in Mice of K-252a Versus K-252a-PEG

The present study has been conducted with the aim of measuring and evaluating the absorption kinetic after dermal administration of K-252a-PEG in mice in comparison to the absorption kinetic of the non conjugated, i.e. non PEGylated, K-252a molecule. The experiment was performed using a dose of active agent in both preparation of 3 mg/kg. For the present study, three subsequent experiments have been performed in vivo using each time 6 Balb/C male mice purchased from Charles River (Calco, Italy). The mice were subdivided in the following experimental groups (two animals per group):

Group 1: The mice were treated with 3 mg/kg of K-252-a, by dermal administration and sacrificed after 30 minutes.

Group 2: The mice were treated with 3 mg/kg of K-252-a by dermal administration and sacrificed after 60 minutes.

Group 3: The mice were treated with 3 mg/kg of K-252-a-PEG(2K) of Example 1 by dermal administration and sacrificed after 60 minutes.

The K-252a and K-252a-PEG(2K) formulations were respectively prepared by dilution of the stock solution (K252a stock solution from Calbiochem batch number 850496, solution of 100 μg/214 μL DMSO; K-252a-PEG(2K) stock solution is a solution of 0.226 mg of K252a/mL DMSO) with olive oil, until a final concentration of K-252a of 0.3 mg/mL olive oil/DMSO 6% was reached. The solutions were respectively prepared as follows: 60 μL K-252a 5 mg/mL DMSO+ 940 μL olive oil and 30 μL K252a-PEG(2K), 5 mg/mL DMSO+470 μL olive oil. The oil-based preparations are in form of emulsions which are rendered homogeneous by repeated sonication. On the back of each animal (shaved with electronic shaver 72 hours before the experiment) 240 μL of the K-252a solution and 235 μL of the K-252a-PEG solution were applied (corresponding to a dose of 3 mg/kg based on an average body weight of the mice of 23-24 g). The applied emulsion was gently massaged on the back of the mice to favor the absorption. The mice were then sacrificed respectively after 30 or 60 minutes under ether anaesthesia and the blood was collected from the ventral aorta with the insulin syringe (approx. 1 mL/animal). The blood was then transferred to an Eppendorf containing 50 μL of an aqueous solution of EDTA 5%. The blood samples were then centrifuged at 2000 g for 5 minutes in a refrigerated (4° C.) centrifuge, purified by solid phase extraction (SPE) and subsequently analyzed through HPLC quantitative analysis (RT-HPLC analysis with)(Terra C18 column, eluent water/ACN).

Figure 4A:
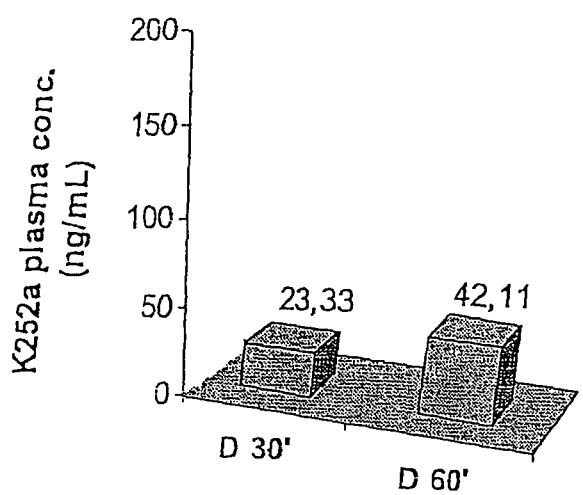

The plasma samples of the mice treated with K-252a showed a certain plasma concentration for both contact periods. The results are shown in FIG. 4, from which it can be gained that the average plasma concentration of K-252a in the mice of group 1, sacrificed after 30 minutes, was 23.33 ng/mL, while the average plasma concentration of K-252a in the mice of group 2, sacrificed after 60, was 42.11 ηg/ml. This shows the occurrence of a systemic adsorption for dermal administration of K-252a. On the other hand, the plasmatic samples of the mice treated with dermal administration of the pegylated conjugate K-252a-PEG(2K) did not show any plasmatic concentration of the active compound even after 60 minutes of contact period. In fact, it was not possible to reveal any chromatographic peak in the plasmatic samples of mice of group 3, even after MALDI-TOF analysis. Hence, no adsorption through the skin of the K-252a-PEG(2K) conjugate was observed after dermal administration.

This data has been confirmed by further experimental studies on a larger group is of tested animals as well as with dermal administration of different dosage amounts of the active agents.

Example 2.2

Pharmacokinetic (PK) Study in Mice: Dermal Single Dose and Repeated Administrations of CT327 Versus K-252a The purpose of this experiment was to evaluate the kinetic of adsorption of CT327 in comparison with K-252a following dermal administration of the two compounds in mice after a single administration as well as the comparative kinetic of the two test compounds after repeated dermal administrations.

Animals: mice (Balb/c males, 7-9 weeks old, Charles River Italia, average body weight of 22.2-22.4 g); 5 experimental groups (control, single and repeated administration of K-252a, single and repeated administration of CT327), 4 animals/group, randomly grouped.

Materials: K-252a (Cephalon lot no 04274F1a), CT327 (Alchemy lot no ALC577.02), Dimethyl sulfoxide (DMSO) Hybri-max® (Sigma lot no 114K2370), White vaseline F.U. (AFOM Medical lot no A908006570), Tween 20 (Sigma lot no 092K0055), $H_2O$ MilliQ, Murine plasma (strain CD1, OF1 lot no 50-18/12/05, supplied by Charles River Laboratories Italia SpA, Calco), Acetonitrile (Merck lot no 1260430545), Methanol (VWR BDH lot no 05Z4034), EDTA (Fluka lot no 393230/1).

Administered dose: K-252a 5.075 mg/kg and CT327 25.27 mg/kg (on the basis of the 78.5% purity, i.e. 32.19 mg/kg, equimolar dosage respect to K-252a) for the single dermal administration; K-252a 1.03 mg/kg and CT327 5.06 mg/kg (on the basis of the 78.5% purity, i.e. 6.45 mg/kg, equimolar dosage respect to K-252a) for the repeated dermal administration (once a day for 5 days).

Administration of the test items: For dermal administration, about 0.25 g of Vaseline cream were spread on the neck of each mouse (shaved the day before starting the experiment, avoiding skin abrasion). Control animals received the vehicle alone at the same dose volume Test article formulation: DMSO 1.1%/white Vaseline cream for single dermal administration and DMSO 0.23%/white Vaseline cream for repeated dermal administration.

Animal sacrifice and blood collection: Blood samples were collected at the following time points after treatment:

Single dermal administration: 1, 3, 6, 9, 18, 24, 36, 48 and 72 hours after administration of K-252a or CT327

Repeated dermal administration: 3 hours and 24 hours after last administration of K-252a and CT327 respectively.

At each sampling time, approximately 0.4 mL blood samples were collected from the ventral aorta of each animal using an insulin syringe, under deep ether anesthesia, and transferred into polyethylene Eppendorf tubes containing 50 μL of 5% EDTA water solution to prevent blood clotting. Blood samples were kept in ice until centrifugation at 1400 g for 5 min. in a refrigerated centrifuge (2-4° C.). From each tube plasma samples were then recovered, put in new Eppendorf tubes and frozen at −20° C. which until the HPLC analysis.

Figure 4B:
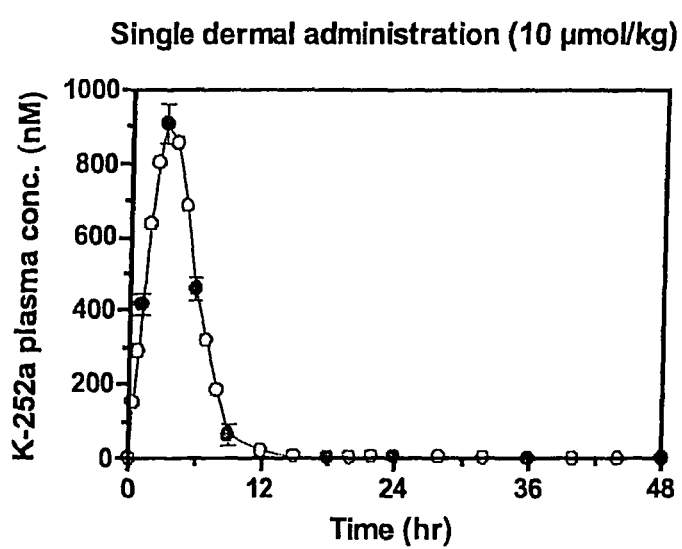

FIG. 4b shows the results of the single dose administration study. The K-252a plasma concentration curve after the single dermal administration of K-252a is shown, reported as mean values±error (95% CI, confidence interval) (4 mice for each time point, analysis in duplicate). Instead, no plasma concentration profile for the CT327 single dermal administration was detected. In fact, the analysis of plasma samples of mice that received a single dermal administration of CT327 at equimolar dosage in comparison to the mice treated with K-252, did not reveal levels of the test compound above the limit of detection (70.6 nM) at any time point.

Computer fitting of the data from each experimental group was then performed by NCOMP version 3.1 program (P. B. Laub et al., Journal of Pharmaceutical Sciences, 1996, 85(4): 393-395). Values for area under the plasma concentration-time profile, $T_{1/2}$, $T_{max}$, $C_{max}$, etc. were calculated by conventional formulas previously described (Gibaldi et al., Pharmacokinetics, 1982, Marcel Dekker, Inc., New York). These PK parameters estimated by fitting the K-252a and CT327 plasma concentration data are listed in the following Table 1.

TABLE 1

Estimated pharmacokinetic parameters in plasma of K-252a and CT327 after single dermal in mice (10 μmol/kg)

| PK parameter | K-252a, derm. | CT327, derm. |
|---|---|---|
| $AUC_{0-\infty}$ (nM · min) | $2.85 \cdot 10^5$ | ND |
| Terminal $T_{1/2}$ (min) | 63.13 | ND |
| $T_{max}$ (min) | 180.00 | ND |
| $C_{max}$ (nM) | 907.98 | ND |

Abbreviations:

$AUC_{0-\infty}$ = area under the curve from time zero to infinity, $T_{1/2}$ = half-life, $C_{max}$ = maximal plasma level, $T_{max}$ = time to maximal plasma level, ND = not detected The results of this study have confirmed that after a single dermal administration K-252a results detectable in plasma at least up to 9 hours after administration (with an half-life of 63 minutes), while CT327 at a dose equivalent to that of K-252a dosage, results undetectable at plasma level up to a contact period of 72 hours.

Table 2 shows the results of the dermal repeated administration study. In particular, Table 2 shows the results of the HPLC analysis of mean plasma levels for the repeated administration of K-252a and CT327. As shown, K-252a exhibits a detectable and quantifiable plasma concentration while, for what CT327 concerns, no detectable level of test compound was revealed in the collected blood after repeated administrations.

TABLE 2

Mean plasma concentrations of K-252a and CT327 after a repeated dermal administration (QD for 5 days) at a dosage of 1.03 mg/kg and 5.06 mg/kg respectively (about 2 μmol/kg)

| Test item and Time point | Mean Plasma Concentration (nM) | 95% CI |
|---|---|---|
| K-252a, t = 3 h | 110.19 | 29.15 |
| CT327, t = 24 h | Not detected | — |

Hence, in this second study, the absorption following a repeated dermal administration (once a day for 5 consecutive days) at a lower dosage (2 μmol/kg) was evaluated. Even in this case no chromatographic peak corresponding to the PEGylated molecule CT327 is detectable in the murine plasma sample. A sufficiently long time point for blood collection (24 h) was chosen in order to put in evidence an eventual very slow absorption. Nevertheless, the present data allow to conclude that no absorption through the skin occurs after dermal administration of K-252a-PEG(2K). Concerning the K-252a compound instead, the resulting K-252a plasma level following 3 hours after the last dermal administration is 110.2 nM, which is even slightly higher if compared to concentration found at same dosage and time point for single dermal administration (72.9 nM±32.5, as value±95% CI).

In conclusion, the results of the present studies confirm the efficacy of polymer conjugation of K-252a in avoiding K-252a systemic absorption either after a single dermal administration at a higher dose or after a 5-day topical treatment at a lower dosage.

Example 3

In Vitro Pharmacology

Example 3.1

In Vitro Studies for Characterising the Antiproliferative Activity of K252a-PEG (2K) as Trka Inhibitor on Human Keratinocytes A metabolic MTT-assay was performed as test of the cellular vitality. The MTT-assay was performed using a well known and validated protocol, whereby the results are quantified through a spectrophotometric lecture, the number of living cells being directly proportional to the quantity of the formazan product formed as reduction product of MTT ([3-(4,5-dimethylthiazol-2-yl)-2,5-diphenyltetrazoliumbromid]) (Mosmann T., Rapid colorimetric assay for cellular growth and survival: Application to proliferation and cytotoxicity assays. J. Immunol. Methods. 1983, Dec. 16, 65(1-2):55-63). In the present study, the MTT-assay was performed on subconfluent cultures of keratinocytes seeded in 96-well plates for cellular culture (8000 cells/well). After the cells have been exposed to the substance which has to be analyzed, the cells are incubated for 4 hours at 37° C. with MTT (0.05%) in serum-free keratinocyte growth medium (KGM Clonetics Corp. San Diego, Calif., USA). After solubilisation of the cells with detergents, the formation of the dyestuff formazan is detected using a spectrophotometer for multi-well plate at 540 nm. The results are given as optical density unit (OD).

Figure 5:
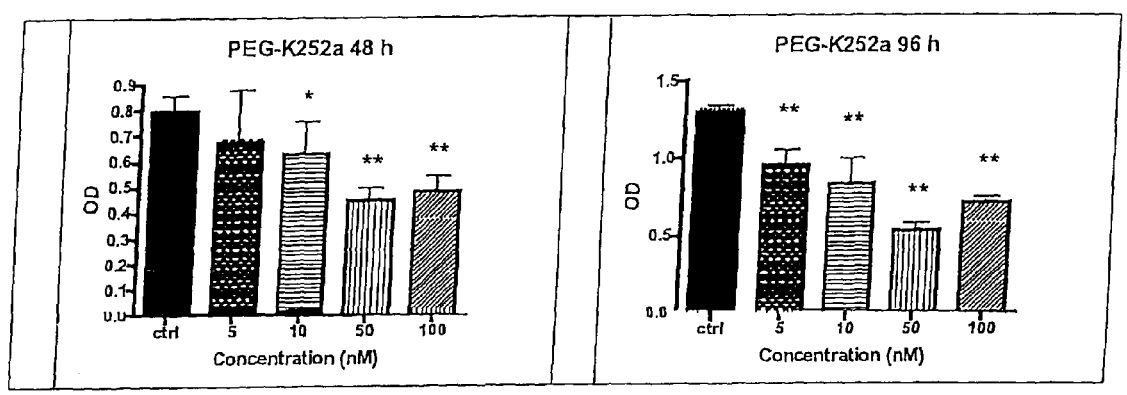
FIG. 5 shows the antiproliferative activity on keratinocytes of the conjugated compound K252a-PEG(2K) in the MTT-assay after 48 and 96 h of contact period.

The antiproliferative activity of the conjugation product K-252a-PEG(2K) was tested with the MTT assay, for a contact time of the isolated keratinocytes in the wells with the solution of the compound to be tested, of 48 h and 96 h respectively and for concentrations of K-252a-PEG(2K) of 5, 10, 50 and 100 nM. All experiments were performed at least three times. The statistical analysis of the results of the MTT assay was performed by using the ANOVA model (the error bars represent the confidence interval 95%, p=0.05). FIG. 5 shows the result of the MTT-assay with K-252a-PEG(2K). It is clearly demonstrated that the K-252a-PEG exhibits an inhibitory action on the keratinocytes for concentrations ≥10 nM after 48 h of contact period, while the inhibitory effect is shown for any concentrations after a period of contact of 96 h.

These results show that the conjugation of K-252a with the polymer PEG does not influence the antiproliferative activity of the active molecule K-252a (FIG. 5). In fact after a period of contact of both 48 h and 96 h an inhibitory action was demonstrated on the proliferation of the keratinocytes.

A further MTT assay analysis was hence performed to prove, that the absence or the delay of systemic absorption of the PEG-conjugated K252a after topical administration (as shown in example 2) and the delayed inhibitory activity on the proliferation of the keratinocytes, could presumably be the result of an delayed entrance of the conjugated K-252a-PEG (2K) compound into the keratinocyte cell, due to conjugation, i.e pegylation.

Therefore further in vitro MIT assay has been performed as described above, both with K-252a and with K-252a-PEG (2K) as compound to be tested, to test the antiproliferative activity of keratinocytes, wherein though the contact times of the active compound with the keratinocytes in the wells have been reduced. The K252a and K-252a-PEG(2K) concentration was 25, 50 and 100 nM respectively. The contact periods were for each concentration 1, 2 and 4 hours respectively. The cell counting was performed after 48 hours and after 96 hours.

The results of the MTT assay with K-252a-PEG(2K) are shown in FIG. 6. Both after 48 h and after 96 h, the effect on keratinocytes proliferation of the conjugated compound K-252a-PEG(2K) does not appear statistically different than the effect obtained with the control sample (FIG. 6a and FIG. 6b).

The same MTT assay was conducted with non conjugated K-252a, the results being shown in FIG. 7a (cell counting after 48 h) and FIG. 7b (cell counting after 96 h). These results have shown a statistically significant antiproliferative action of K-252a, for any contact time, at concentration z 200 nM and at a cell counting after 48 h. When performing the cell counting after 96 h an antiproliferative activity is even obtained for any tested concentration and any contact time.

FIG. 8 shows a comparison of the data of the inhibitory activity of 100 nM K-252a and of K-252a-PEG(2K) respectively for the above described MTT assay with a contact time of 4 hours and a cell counting performed after 96 hours.

These results reveal that, contrary to the non conjugated K-252a compound, a contact time of 4 hours is not sufficient for K-252a-PEG(2K) to evolve its antiproliferative action for concentrations ≤100 nM (even when cell counting is exploited after 96 h). In compare to the non conjugated, i.e. non pegylated K-252a, for lower concentrations of K-252a-PEG(2K) a longer period of contact is required to obtain the desired inhibition effect on the proliferative activity of keratinocytes. For K-252a-PEG(2K) a clear delay in its capacity of entering into the cell and therefore a delay in passing the cellular membrane has hence been shown, resulting from pegylation of the K-252a molecule.

This seems further to confirm the hypothesis that K-252a compound and its derivatives exploit their activity after intracellular accumulation of the K-252a compound and its derivatives and subsequent slow release of the active molecules even after removal of the culture medium.

Example 3.2

In Vitro Evaluation of the Kinase Inhibition Profile for K-252a and CT327

It is well known in literature that K-252a is a potent inhibitor of several kinases. In the present study, the inhibitory activity of K-252a against selected common tyrosine kinases and serine/threonine kinases was evaluated. A similar experiment has been conducted for evaluating the inhibitory activity of CT327.

K-252a (Acros lot A020265401) was dissolved in DMSO to make a 1 mM stock solution which was then diluted with DMSO to obtain a 20 μM solution, further diluted with the assay buffer to achieve a concentration of 0.8 μM. K-252a was tested at a concentration of 200 nM. The preparation of CT327 and the reference compounds was conducted following a similar procedure. CT327 also was tested at a concentration of 200 nM. As reference compounds of the invention protein kinase inhibitors well known in the art, such as staurosporine, 5-iodotubericidin, NK inhibitor II and SB202190 (as shown in Table 3) have been used.

TABLE 3

Reference compounds

| Reference Compounds | Concentration (nM) | Kinases |
|---|---|---|
| Staurosporine | 0.3–10000 | Tyrosine kinases |
|  |  | Other serine/threonine kinases |
| 5-Iodotubericidin | 10000 | ERK1, ERK2 |
| JNK Inhibitor II | 300 | JNK1, JNK2 |
| SB202190 | 300 | p38α, p38β |

The kinase inhibition studies for K-252a and C327 have been performed using standard assays for the respective kinase.

The results of the tyrosine kinase inhibition and serine/threonine kinases inhibition for K-252a are shown in the Table a and b, respectively, reported in FIG. 9a. The inhibitory activity of CT327 against the tested tyrosine kinase and serine/threonine kinases is shown in the Table a and b, respectively, reported in FIG. 9b. The readout value of reaction control (with ATP) was set as a 0% inhibition and the readout value of background (without ATP) was set as a 100% inhibition.

K-252a showed at a concentration of 200 nM a very strong inhibitory activity of greater than 90% against 16 of the tested kinases (TNK1, JAK2, JAK3, TYK2, FLT3, PDGFRα, PDGFRβ, RET, TrkA, TrkB, TrkC, CHK1, CHK2, JNK1, JNK2, AurA and MAP2K3) and a strong inhibition between 80% and 90% against further 7 of the tested kinases (MER, JAK1, MET, KIT, BLK, FGR and CaMK2a).

On the contrary, CT327 showed, at an equivalent concentration in comparison to K-252a (200 nM), a strong inhibitory activity (>50%) only against TrkA within the tyrosine kinases tested. A low activity was shown by CT327 against JAK2, JAK3 and FLT3 (between 20% and 30%), while a very low activity was seen against TNK1, EphB4, PDGFRβ, BLK, LCK, TrkB and TrkC (between 10% and 20%). No inhibition at all was observed for the majority of the tested tyrosine kinases.

Within the serine/threonine kinases, CT327 showed a strong inhibitory activity (>40%) only against MAP2K3, very low (14%) against JNK3 (highlighted in green) and no inhibitory activity at all against the other serine/threonine kinases tested.

FIG. 10 reports the comparison of the selectivity of CT327 versus K-252a. The results clearly show a dramatic improvement in the selectivity of kinase inhibition of CT327 versus K-252a. In particular, the results demonstrate an increase selectivity in kinase activity of CT327 with respect to TrkA in the group of the tyrosine kinases and with respect to MAP2K3 in the group of the serine/threonine kinases.

These data suggest that the inhibition selectivity of CT327 is in particular directed to the main targets TrkA and MAP2K3, with the consequent potential decrease of undesired biological effects as consequence from the inhibition activity against other kinases. Hence, the less other kinases are inhibited, the less toxic the molecule is likely to be.

In sum, the results of the studies described in the Examples 2 and 3 make the polymer conjugates of K-252a of formula (I), and in particular the K-252a-PEG (2K), promising candidates as active agents in a medicament, due to the intact biological activity and the concomitant reduced risk of adverse effects.

Example 3.3

In Vitro Evaluation of the $IC_{50}$ Against TRKA for K-252a and CT327

The purpose of this study was to measure $IC_{50}$ values for CT327 and K-252a against TrkA kinase. Test compound solutions were diluted with DMSO to achieve 100-fold lower concentration and then further 25-fold diluted with the assay buffer (15 mM Tris-HCl, pH 7.5, 0.01% Tween-20, 2 mM DTT) to obtain the final test solutions. CT327 and K-252a were tested at the following concentrations: 1000 nM, 300 nM, 100 nM, 30 nM, 10 nM, 3 nM, 1 nM, 0.3 nM, 0.1 nM, 0.03 nM. Preparation of reference compound (Staurosporine) was conducted with a method similar to the one used for the preparation of the test compounds. Staurosporine was tested at the following concentrations: 100 nM, 30 nM, 10 nM, 3 nM, 1 nM, 0.3 nM, 0.1 nM, 0.03 nM, 0.01 nM and 0.003 nM. The assay procedure is the following:

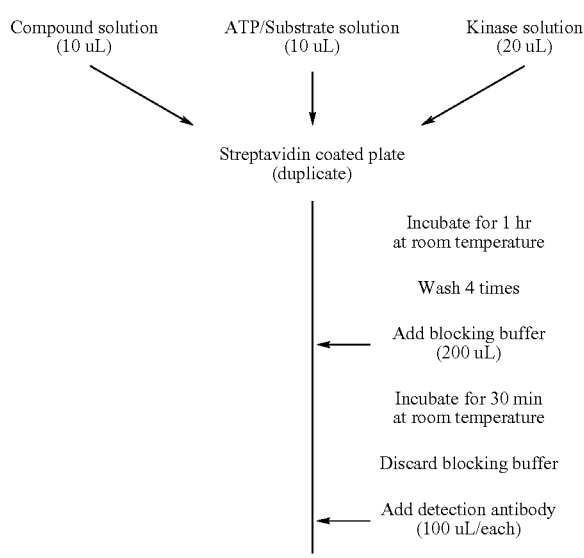

-continued

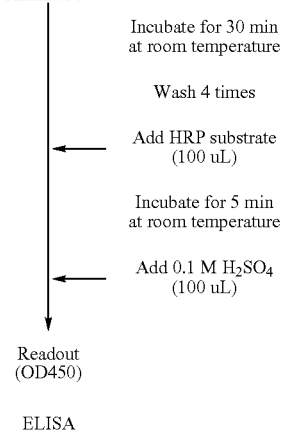

ELISA

Readout value of reaction control (with ATP) was set as a 0% inhibition, and readout value of background (without ATP) was set as a 100% inhibition, then a the percent inhibition of each test solution was calculated. $IC_{50}$ value was calculated from concentration versus % inhibition curves by fitting to a four parameter logistic curve.

$IC_{50}$ values of K-252a and CT327 against TrkA were 0.50 nM and 186 nM, respectively. The corresponding $IC_{50}$ value of reference compound (Staurosporine) against TrkA was 0.12 nM. These results are summarized FIG. 11.

Example 4

Acute Single Dose Toxicity Study in Mice for CT327 Versus K-252a

The purpose of this study was to perform a non-clinical toxicity study, in order to evaluate the toxicity of CT327 when administered as a single dose in mice by the intraperitoneal route and by oral administration, in comparison with its precursor K-252a. A total of 70 mice (Balb/c, 35 males and 35 females) where divided in 14 sub-groups (7 groups composed by 5 males and 7 groups composed by 5 females) to receive the following dose levels of test items:
K-252a: 30, 45, 60, 75, and 90 mg/Kg
CT327: 316.68 and 475.02 mg/Kg (corresponding to 60 and 90 mg of K-252a, respectively).

Observations, which included clinical signs and behavioral changes, were performed every 30 minutes in the first 6 hour following administration, and twice a day during the following 7 days.

Among the male groups treated with K-252a, only those administered with the lowest dose (30 mg/Kg) survived, while all the others were found dead within the first 22 hours after dosing. The resulting $LD_{50}$ was 37.74 mg/kg.

Also the female mice administered with the lowest K-252a dose survived and, like males given the same dose, showed very mild/mild sedation which disappeared within 8-10 hours. One female survived out of the five given 45 mg/kg and one among those which received 60 mg/kg. Higher doses of K-252a were lethal to all female mice. The $LD_{50}$ for females was 41.44 mg/kg. The average $LD_{50}$ for males and females together was therefore 39.02 mg/kg.

Doses of CT327 equal to 316.68 and 475.02 mg/kg, corresponding to 60 and 90 mg/kg of K-252a respectively, did not induce any behavioral and/or clinical sign of toxicity in any of the groups treated, either within the hours immediately following dosing or during the 7 day of the observation period.

Similar results have been obtained following oral administration. In particular, $LD_{50}$ for K-252a has been found to be 78 mg/kg, whereas no mortality has been observed up to the maximum dose of 790 mg/kg of CT327.

Example 5

A study was performed with the purpose to quantitatively determine a panel of 24 cytokines in the plasma of mice at different time points after LPS-induced endotoxemia and to compare the profiles obtained with those of CT327 pretreated endotoxemic mice.

Protocol of the Study:

The animals were divided into two experimental groups (55 mice/group) that were treated following this schedule:

|  | CONTROL (n = 55) | TREATED (n = 55) |
| --- | --- | --- |
| Time: −15 minutes | Vehicle | CT-327 (105.56 mg/kg; ip) |
| Time: 0 | LPS (4 mg/kg; i.p.) | LPS (4 mg/kg; i.p.) |

Endotoxemia Induction:
At time 0 both groups received a dose of LPS corresponding to 4 mg/kg, i.p.

CT327 Treatments:
The "treated" experimental group received a single dose of CT327 corresponding to 105.56 mg/kg, i.p. This dose was administered 15 minutes before LPS endotoxemia induction (time 0). At the same time the "control" group received an equivalent volume of vehicle solution.

Each experimental group was divided in 11 sub-groups with 5 mice/sub-group. Each sub-group was sacrificed at different time points and blood samples collected.

Time points for blood sample collection were:
Time: time 0 (basal); before LPS treatment
Time: +30 minutes; after LPS treatment
Time: +1 hours; after LPS treatment
Time: +2 hours; after LPS treatment
Time: +3 hours; after LPS treatment
Time: +6 hours; after LPS treatment
Time: +12 hours; after LPS treatment
Time: +18 hours; after LPS treatment
Time: +24 hours; after LPS treatment
Time: +48 hours; after LPS treatment
Time: +72 hours; after LPS treatment Blood samples were collected in sodium citrate tubes (100 μl sodium citrate 0.1 M/900 μl of blood) and centrifuged at 1000 g at 4° C. for 10 minutes. Plasma samples were collected and 50 μl/sample were frozen at −80° C. until testing for multiple cytokines profiling. The samples were analyzed in double through the Bio-Plex System (Bio-Rad) by using the 23-plex panel at the Dept. of Genetics, Biology and Biochemistry, Torino University, led by Prof. Silengo. Plasma levels of the following cytokines were determined: IL-1a, IL-1b, IL-2, IL-3, IL-4, IL-5, IL-6, IL-10, IL-12(p40), IL-12(p70), IL-17, G-CSF, GM-CSF, IFN-γ, KC, MIP-1-α, RANTES, TNF-α, IL-9, IL-13, eotaxin, MCP-1, MIP-1-α.

The most significant results are shown in FIGS. 12 and 13 In particular FIG. 12 shows the significant reduction of TNF-α secretion in the plasma levels of mice pre-treated with the CT327 compound according to the invention.

FIGS. 13a-e show instead to the results of the parallel experiment done with K-252a. A significant reduction not only of TNF-α, but also of IFN-γ, MCP-1, MIP-α and RANTES.

Example 6

Synthesis of a K-252a-PEG(1100) (Compound CT336)

1) m-PEG$_{1100}$-O—CH—COOEt Synthesis

In suitable reaction flask under an inert atmosphere t-BuOK (11.2 g, 100.0 mmol) was added to anhydrous THF (70.0 mL) at room temperature under stirring.

When dissolution was complete MeO-PEG$_{100}$-OH (22.0 g, 20.0 mmol) was added and then BrCH$_2$CO$_2$Et (16.7 g, 100.0 mmol) was added dropwise within 30 min and the reaction flask was cooled with a water bath.

After 2 h the solvent was removed under vacuum at 40° C.

The obtained residue (ca 65 g) was dissolved in H$_2$O (100 mL) and the solution rapidly extracted with of CH$_2$Cl$_2$ (3×100 mL). The organic layer was anhydrified (Na$_2$SO$_4$) and the solvent removed under vacuum at 40° C.

2) m-PEG$_{1100}$-O—CH$_2$—COOH Synthesis

The crude m-PEG-O—CH$_2$—COOEt (ca 20 g) obtained as above described was dissolved in aqueous NaOH (1 N, 200 mL) and heated at 60° C. for 3 h under stirring.

The reaction mixture was then acidified to pH 3 using aqueous HCl (1 N, ca 165 mL) and then partitioned with CH$_2$Cl$_2$ (5×100 mL). The collected organic extracts were anhydrified (Na$_2$SO$_4$) and the solvent removed under vacuum at 40° C.

The resulting viscous oil (ca 18 g) was dropped into cold anhydrous Et$_2$O (75 mL), and the white precipitate filtered, collected and the residual solvent evaporated under vacuum at room temperature (15 g).

3) m-PEG$_{1100}$-O—CH$_2$,—NCO Synthesis

In a suitable reaction flask, m-PEG$_{1100}$-O—CH$_2$—COOH (10.0 g, 9.1 mmol) was dissolved in toluene (80 mL) under stirring. About 15 mL of solvent were then distilled off in order to dry the mixture by azeotropic distillation.

The residue was cooled to room temperature and anhydrous Et$_3$N (1.1 g, 10.9 mmol) and diphenyl phosphoryl azide [(C$_6$H$_5$O)$_2$P(O)N$_3$] (2.7 g, 10.0 mmol) were successively added.

After 30 min at room temperature the mixture was heated to reflux for 2 h, then the solvent evaporated under vacuum at 60° C.

The resulting viscous oil (ca 9 g) was dropped into cold anhydrous Et$_2$O (200 mL), the white precipitate filtered, collected and the residual solvent removed under vacuum at room temperature (6.0 g).

4) Synthesis of a K-252a-PEG$_{1100}$ Conjugate

A 1 mg/mL solution of K-252a in DCM was prepared dissolving 1.5 mg of K-252a (corresponding to 3.2 μmol) in 1.5 mL of CH$_2$Cl$_2$ by gentle stirring. The solution was added into a glass flask containing 38.06 mg (32.5 μmol) of m-PEG$_{1100}$-O—CH$_2$—NCO and 100 μL of a 32.8 mg/mL triethylamine solution in CH$_2$Cl$_2$ as basic catalyst. Both the polymer and the catalyst were used in a 10-fold molar ratio compared to K-252a. The mixture was kept at room temperature under magnetic stirring (spin rate about 500 rpm) and gentle nitrogen flux overnight (reaction time=16 h 40'). The solution was then evaporated and the solid residue was treated with 300 μL of DMSO. The mixture was purified by RP-HPLC on a C18 column in order to obtain the desired product (peak corresponding to about 61/39 ACN/H$_2$O gradient). The corresponding fractions of four subsequent purification processes were pooled and dried by ACN evaporation and then freeze-dried. A MALDI-TOF analysis confirmed the identification of the product with the K-252a-PEG$_{1100}$ conjugate.

The invention claimed is:

1. A polymer conjugate of formula (III):

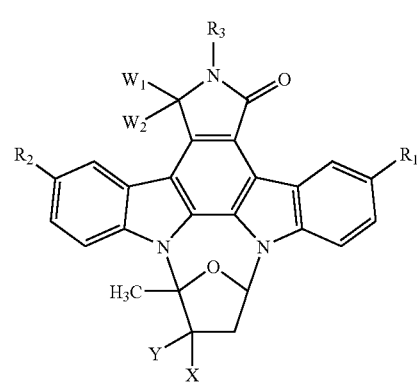

Formula (III)

wherein R$^1$ and R$^2$ are hydrogen,

R$^3$ is hydrogen, halogen, aryl, carbamoyl, substituted or unsubstituted lower alkyl, substituted or unsubstituted alkenyl, substituted or unsubstituted lower alkynyl or amino;

W$^1$ and W$^2$ are hydrogen,

X represents -L$^1$-X' and Y represents -L$^2$-Y' wherein at least one of X' and Y' is a polymer, either linear or branched, which is bound by L$^1$ and/or L$^2$ to the tetrahydrofuran ring of the compound of formula (III); L$^1$ and/or L$^2$ are a covalent chemical bond or a linker group;

when Y' is a polymer, and X' is not a polymer, L$^1$ is a covalent chemical bond and X' is selected from the group consisting of (a) hydrogen, lower hydroxyalkyl, acyl, carboxy, lower alkoxycarbonyl, (b) —CONR$^{17a}$R$^{17b}$, wherein R$^{17a}$ and R$^{17b}$ are each independently selected from (i) hydrogen, lower alkyl, lower alkenyl, lower alkynyl, (ii) —CH$_2$R$^{18}$; wherein R$^{18}$ is hydroxy, and (iii) —NR$^{19}$R$^{20}$, wherein R$^{19}$ or R$^{20}$ are each independently hydrogen, lower alkyl, lower alkenyl, lower alkynyl or R$^{19}$ or R$^{20}$ are independently the residue of an α-amino acid in which the hydroxy group of the carboxyl group is excluded, or R$^{19}$ or R$^{20}$ are combined with a nitrogen atom to form a heterocyclic group; and (c) —CH═N—R$^{21}$, wherein R$^{21}$ is hydroxy, lower alkoxy, amino, guanidino, or imidazolylamino;

when X' is polymer, and Y' is not a polymer, L$^2$ is a covalent chemical bond and Y' is hydroxy, lower alkoxy, aralkyloxy, or acyloxy;

or a pharmaceutically acceptable salt thereof.

2. The polymer conjugate of claim 1, wherein the polymer is polyethylene glycol (PEG) or methoxy-polyethylene glycol (m-PEG).

3. The polymer conjugate of claim 1, wherein the polymer is a polymer having a molecular weight from 100 to 100 000 Da.

4. The polymer conjugate of claim 2, wherein the polymer is PEG or mPEG with an average molecular weight of 2000 Da or 5000 Da.

5. The polymer conjugate of claim 2 the polymer is PEG or mPEG with an average molecular weight of 550 Da or 1100 Da.

6. The polymer conjugate of claim 1, wherein the covalent chemical bond between polymer and compound of formulae (I) or (II) or wherein the $L^1$ and/or $L^2$ of formula (III) is a carbamate, an ether, an ester, a carbon, an amide and/or an amine bond.

7. The polymer conjugate of claim 1, wherein $R_1$, $R_2$, $R_3$, $W_1$, and $W_2$ are hydrogen, Y' is a polymer and X' is methoxycarbonyl or carboxyl.

8. The polymer conjugate of claim 7, wherein $L^2$ is an ether or carbamate bond.

9. The polymer conjugate of claim 1, wherein $R_1$, $R_2$, $R_3$, $W_1$, and $W_2$ are hydrogen, X' is a polymer and Y' is hydroxy.

10. The polymer conjugate of claim 9, wherein $L^1$ is an amine or amide bond.

11. The polymer conjugate of claim 3 for use as an active agent in a medicament.

12. The polymer conjugate of claim 11 for use as an active agent in a topical medicament.

13. The polymer conjugate of claim 11 for use as an active agent in a medicament for systemic treatment.

14. Pharmaceutical composition comprising at least one polymer conjugate of claim 1, optionally together with pharmaceutically acceptable carriers, adjuvants, diluents or/and additives.

15. The pharmaceutical composition of claim 14 for diagnostic application.

16. The pharmaceutical composition of claim 14 for therapeutic application.

17. The polymer conjugate according to claim 1, wherein said conjugate is selected from the group consisting of CT327, CT335, CT339, and CT340.

* * * * *